(12) United States Patent
Danowski et al.

(10) Patent No.: US 7,382,263 B2
(45) Date of Patent: Jun. 3, 2008

(54) ORAL DRUG COMPLIANCE MONITORING USING RADIO FREQUENCY IDENTIFICATION TAGS

(75) Inventors: Kristine L. Danowski, Dallas, TX (US); Larry S. Sun, Lake Jackson, TX (US); Peter K. Mercure, Midland, MI (US); Robert P. Haley, Midland, MI (US); Douglas P. White, Lake Jackson, TX (US); Michelle A. Pressler, Roscoe, IL (US); Susan J. Babinec, Midland, MI (US); Flor A. Castillo, Lake Jackson, TX (US); Jahne Simon, Angleton, TX (US); Paul E. Cranley, Lake Jackson, TX (US); Malcolm W. Warren, II, Sanford, MI (US); Diedre A. Strand, Midland, MI (US); Bettina M. Rosner, San Diego, CA (US); Robert B. Fletcher, Midland, MI (US); Christopher M. Jones, Midland, MI (US); Thomas H. Kalantar, Midland, MI (US); Mark T. Bernius, Midland, MI (US); W. Chris McDougall, Midland, MI (US); Mark S. B. Felix, Uitikon Waldegg (CH)

(73) Assignee: Dow Global Technologies Inc., Midland, MI (US)

( * ) Notice: Subject to any disclaimer, the term of this patent is extended or adjusted under 35 U.S.C. 154(b) by 225 days.

(21) Appl. No.: 11/436,917

(22) Filed: May 18, 2006

(65) Prior Publication Data

US 2006/0289640 A1 Dec. 28, 2006

Related U.S. Application Data

(60) Provisional application No. 60/683,141, filed on May 20, 2005, provisional application No. 60/760,903, filed on Jan. 20, 2006.

(51) Int. Cl.
*G08B 13/14* (2006.01)
*G08B 23/00* (2006.01)
*A61B 19/00* (2006.01)
*A61N 5/00* (2006.01)

(52) U.S. Cl. .............. 340/572.1; 340/572.7; 340/573.1; 128/899; 604/890.1; 600/3; 600/309

(58) Field of Classification Search ............. 340/572.1, 340/572.4, 572.7, 572.8, 573.1; 128/899; 604/21, 890.1, 891.1, 93.01, 892.1; 600/2, 600/3, 7, 309, 424; 235/380, 487
See application file for complete search history.

(56) References Cited

U.S. PATENT DOCUMENTS 4,844,076 A 7/1989 Leslo et al.
(Continued)

FOREIGN PATENT DOCUMENTS

WO WO 1998/19619 5/1998
(Continued)

OTHER PUBLICATIONS

Greenberg, Clinical Therapeutics, 6(5): 592-599. 1984.
(Continued)

*Primary Examiner*—Toan N. Pham

(57) ABSTRACT

A device useful for oral drug delivery device consisting of: (a) a capsule, tablet or pill designed to disperse in the gastrointestinal system; (b) an RFID tag positioned in the capsule, tablet or pill, the RFID tag comprising an antenna; (c) an object selected from the group consisting of a magnet, a ferromagnetic object, a ferrite object and an electromagnetic shielding object positioned within, over or adjacent the antenna of the RFID tag to alter the antenna characteristics of the RFID tag so that if the RFID tag is interrogated before the capsule, tablet or pill disperses in the gastrointestinal system, the response of the RFID tag is sufficiently altered or attenuated to determine that the capsule, tablet or pill has not dispersed in the gastrointestinal system and so that if the RFID tag is interrogated after the capsule, tablet or pill has dispersed in the gastrointestinal system, the object separates from the RFID tag so that the response of the RFID tag is sufficiently detectable to determine that the capsule, tablet or pill has dispersed in the gastrointestinal system. Alternatively, a switch can be used to signal ingestion of the device, and change the response of the device.

11 Claims, 25 Drawing Sheets

U.S. PATENT DOCUMENTS

| | | | |
|---|---|---|---|
| 5,079,006 A | | 1/1992 | Urquhart |
| 5,170,801 A | * | 12/1992 | Casper et al. ............... 600/582 |
| 5,279,607 A | | 1/1994 | Schontag et al. |
| 6,294,997 B1 | | 9/2001 | Paratore et al. |
| 6,366,206 B1 | | 4/2002 | Ishikawa et al. |
| 6,440,069 B1 | * | 8/2002 | Raymond et al. ........... 600/300 |
| 6,632,175 B1 | * | 10/2003 | Marshall .................... 600/309 |
| 6,663,846 B1 | | 12/2003 | McCombs et al. |
| 6,776,165 B2 | * | 8/2004 | Jin ............................. 128/899 |
| 6,927,687 B2 | | 8/2005 | Carrender |
| 6,950,028 B2 | | 9/2005 | Zweig |
| 7,282,045 B2 | * | 10/2007 | Houzego et al. ......... 604/890.1 |
| 2002/0145525 A1 | | 10/2002 | Friedman et al. |
| 2003/0117787 A1 | | 6/2003 | Nakauchi |
| 2004/0081587 A1 | | 4/2004 | Melker et al. |
| 2004/0223481 A1 | | 11/2004 | Juels et al. |
| 2005/0031536 A1 | | 2/2005 | Grycznski et al. |
| 2005/0174236 A1 | | 8/2005 | Brookner |
| 2006/0044178 A1 | | 3/2006 | Miller, Jr. et al. |

FOREIGN PATENT DOCUMENTS

| | | |
|---|---|---|
| WO | WO 01/22377 | 3/2001 |
| WO | WO 2003/076953 | 9/2003 |
| WO | WO 2003/098175 | 11/2003 |
| WO | WO 2004/014670 | 2/2004 |
| WO | WO 2004/023389 | 3/2004 |
| WO | WO 2004/051985 | 6/2004 |
| WO | WO 2005/043100 | 5/2005 |
| WO | WO 2005/092012 | 10/2005 |

OTHER PUBLICATIONS

Vrijens and Goetghebeur, Statist. Med. 23, 531-544, 2004).
Stone et al., Control Clin. Trials. 24, 182-199, 2003).
Coutts et al., Arch. Dis. Child. 67, 332-333, 1992.
Rand et al, Am. Rev. Respir. Dis. 146, 1559-1564, 1992.
Rudd et al, Clin. Pharmacol. Therap. 46, 169-176, 1989.
Simmons et al, Chest. 118, 290-295, 2000.
Insuil, W., Controlled Clinical Trials, 5:451-458, Workshop (1985).
Urquhart, John and De Klerk, Erik, Statistics in Medicine, vol. 17, 251-267. (1998).
Urquhart John, British Journal of Clinical Pharmacology, 54(2), 212-20, 2000.
Noeller, H.G. German Medical Monthly, 6:3, 1961.
Noeller, H.G., German Medical Monthly, 6,3 1961/.
Kashyap, N., et al., Drug Delivery Technology, 32., 2004.
A. Lambert, et al., Autonomous telemetric Capsule to explore the small bowel, Medical & Biological Engineering & Computing, 29(1991).

* cited by examiner

ORAL DRUG COMPLIANCE MONITORING USING RADIO FREQUENCY IDENTIFICATION TAGS

CROSS-REFERENCE TO RELATED APPLICATIONS

This application claims the benefit of U.S. Provisional Application Nos. 60/683,141, filed May 20, 2005, and 60/760,903 filed Jan. 20, 2006.

BACKGROUND OF THE INVENTION

The instant invention relates to oral drug compliance monitoring, and, more particularly, to the use of radio frequency identification tags ingested by the patient with a drug formulation.

Non-compliance of patients to drug regimens prescribed by their physicians results in increased cost of medical care, higher complication rates, as well as drug wastage. Non-compliance refers to the failure to take the prescribed dosage at the prescribed time which results in undermedication or overmedication. In a survey of 57 non-compliance studies, non-compliance ranged from 15% to as high as 95% in all study populations, regardless of medications, patient population characteristics, drug being delivered or study methodology (Greenberg, Clinical Therapeutics, 6(5):592-599, 1984).

In the clinical drug stage, accurately measuring compliance can lead to benefits such as: improved statistical reliability of a clinical study; clinical studies being completed sooner; and a determination of the effect of non-compliance as a function of the degree of non-compliance. In the therapeutic stage, accurately measuring compliance has a number of important benefits such as: warning a patient about the potential for developing a drug resistant infection related to poor compliance; and identifying a side effect of a drug related to overdosing.

Compliance to the instructions given to patients during any clinical trial is usually less than 50% in relatively short-term and less than 40% in longer-term trials using traditional methods (e.g., paper diaries) for making entries to show compliance (Vrijens and Goetghebeur, Statist. Med. 23, 531-544, 2004). A clinical trial on chronic pain patients reported only an 11% compliance with as high as 80% fake entries when paper diaries secretly instrumented to tract diary usage were given to patients (Stone et al., Control Clin. Trials. 24, 182-199, 2003) wherein on 32% of study days the paper diary was not opened, yet the compliance entries for those days exceeded 90%. A high incidence of intentional dumping of medications prior to the clinic visit by removing all or most of the medication at one time also occurs in clinical studies (Coutts et al, Arch. Dis. Child. 67, 332-333, 1992; Rand et al, Am. Rev. Respir. Dis. 146, 1559-1564, 1992; Rudd et al, Clin. Pharmacol. Therap. 46, 169-176, 1989; Simmons et al, Chest. 118, 290-295, 2000). Thus, deception among noncompliant patients occurs frequently in clinical trials, and is not often revealed by the traditional monitoring methods. The result is generation of data difficult to interpret and, worse, useless to reliably predict the effectiveness of clinical trials. Better monitoring of the time of actual drug intake will help alleviate many of these issues. For example, blood levels of a drug can be corrected for the time of actual drug intake for better pharmacokinetic/pharmacodynamic interpretations than relying on the time when patient(s) was instructed to take the medication. However, most of the present tracking devices that are utilized in clinical trials only track the initiation of the process of drug intake, i.e., by tracking the time the drug containers are opened or activated. In order to more accurately monitor the compliance of a clinical trial, a more sophisticated method of monitoring the drug intake is needed.

Confirmation of drug compliance by way of direct observation by trained persons is effective but impractical in most situations. Confirmation of drug compliance by blood or urine analysis is also impractical in most situations. Transdermal detection devices attached to the skin of a patient have been developed which detect ingested drug components through the skin and such devices can transmit a signal to a remote receiver at an external site such as a healthcare facility, see U.S. Pat. No. 6,663,846 and USPAP 2005/0031536. Electronic sensor systems have been developed which detect ingested drug components in the breath of a patient, see USPAP 2004/0081587. Radio frequency identification (RFID) tags have been incorporated into drug pills, each tag capable of identifying the type of medication, its dosage, and its lot number by way of a unique code emitted by the tag when interrogated by a corresponding radio frequency "reader", see U.S. Pat. No. 6,366,206. The RFID of the '206 patent can incorporate a biosensor that detects, for example, a change in pH to determine whether the pill has dissolved and exposed the RFID tag to the environment of the gastrointestinal system. The technology of the '206 patent requires a highly specialized spherical RFID semiconductor and biosensor. It would be an advance in the art if RFID technology could be used in a less complex manner.

SUMMARY OF THE INVENTION

The instant invention is a solution, at least in part, to the above stated problems. The instant invention provides a number of new and improved alternatives for determining drug compliance using RFID tags.

More specifically, the instant invention is a device useful for oral drug delivery, comprising: (a) a capsule, tablet or pill designed to disperse in the gastrointestinal system; (b) an RFID tag positioned in the capsule, tablet or pill, the RFID tag comprising an antenna; (c) an object selected from the group consisting of a magnet, a ferromagnetic object, a ferrite object and an electromagnetic shielding object positioned within, over or adjacent the antenna of the RFID tag to alter the antenna characteristics of the RFID tag so that if the RFID tag is interrogated before the capsule, tablet or pill disperses in the gastrointestinal system, the response of the RFID tag is sufficiently altered or attenuated to determine that the capsule, tablet or pill has not dispersed in the gastrointestinal system and so that if the RFID tag is interrogated after the capsule, tablet or pill has dispersed in the gastrointestinal system, the object separates from the RFID tag so that the response of the RFID tag is sufficiently detectable to determine that the capsule, tablet or pill has dispersed in the gastrointestinal system.

In another embodiment, the instant invention is a device useful for oral drug delivery, comprising: (a) a tablet, pill or capsule designed to disperse in the gastrointestinal system; (b) an RFID tag positioned in the tablet, pill or capsule, the RFID tag comprising a switch, the switch turning on or off in response to conditions in the gastrointestinal system so that if the RFID tag is interrogated before the tablet, pill or capsule disperses in the gastrointestinal system, the response of the RFID tag signifies that the capsule has not dispersed in the gastrointestinal system and so that if the RFID tag is interrogated after the tablet, pill or capsule disperses in the gastrointestinal system, the response of the RFID tag signifies that the tablet, pill or capsule has dispersed in the gastrointestinal system.

In another embodiment, the instant invention is a device useful for oral drug delivery, comprising: (a) a capsule, tablet or pill designed to disperse in the gastrointestinal system; (b) a first non-anti-collision RFID tag positioned in the capsule; (c) a second non-anti-collision RFID tag positioned in the capsule, so that if the RFID tags are interrogated by an RFID reader before the capsule, tablet or pill disperses in the gastrointestinal system, the response of the RFID tags collide and so that after the dispersible material of the capsule has dispersed in the gastrointestinal system thereby allowing the first and second non-anti-collision tags to separate from each other, then the response of the RFID tags is sufficiently different from each other to determine that the capsule has dispersed in the gastrointestinal system.

DETAILED DESCRIPTION

Figure 1:
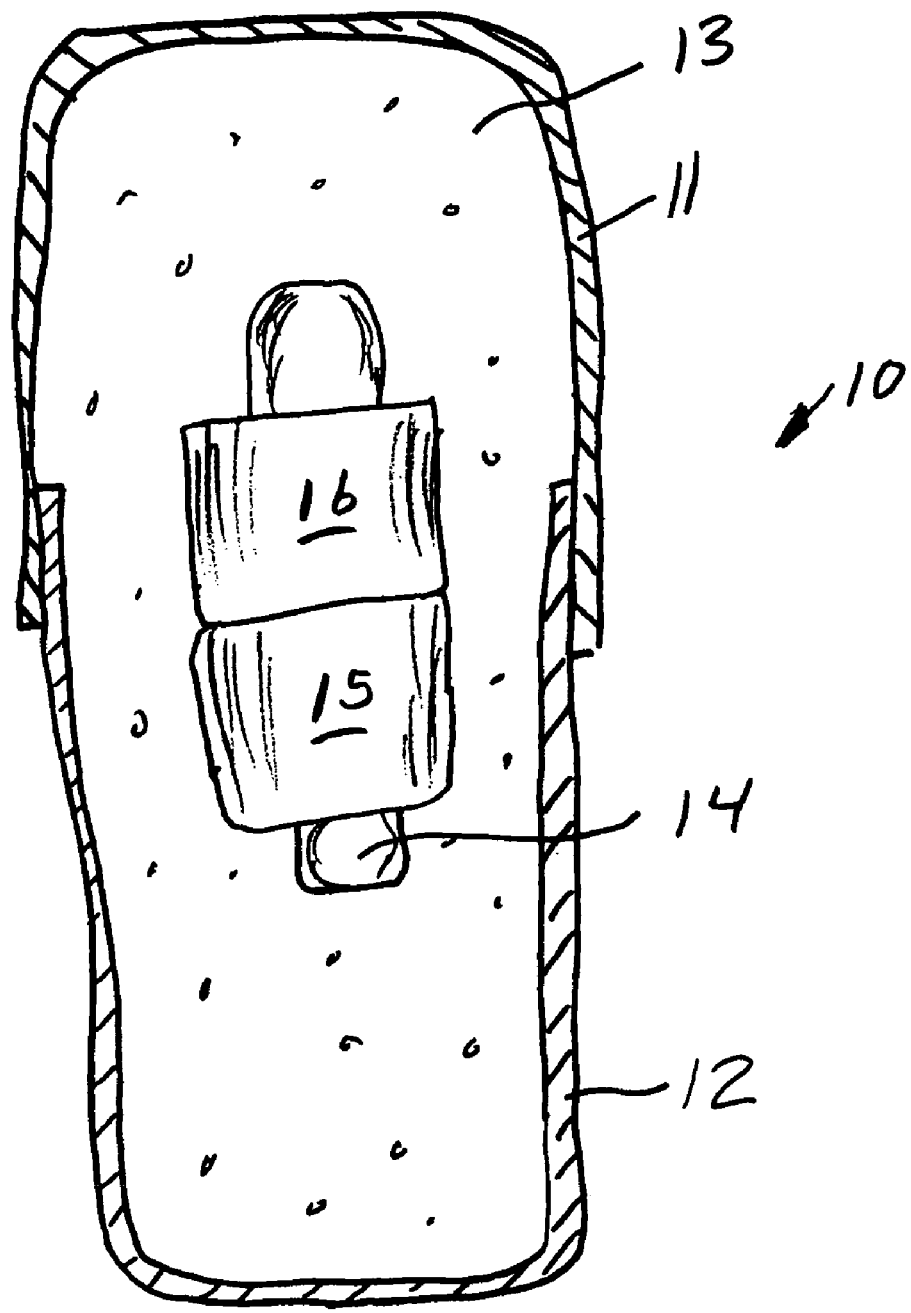
FIG. 1 is an enlarged view, part in cross-section and part in full, of an oral drug delivery system comprising a gelatin capsule containing a pair of ferrite rings over an RFID tag.

Referring now to FIG. 1, therein is shown an oral drug delivery system 10 of the instant invention, comprising an upper gelatin capsule portion 11 and a lower gelatin capsule portion 12. A Texas Instruments low frequency RFID tag 14 is positioned within the capsule of the system 10. The tag 14 is encapsulated in glass and includes an RFID chip encoded to identify a drug type, dose, lot number etc. The tag 14 includes an antenna. The remaining volume within the capsule of the system 10 is, of course, available to contain a drug formulation 13. A pair of ferrite rings 15 and 16 are positioned around the RFID tag 14 to alter the antenna characteristics of the RFID tag so that if the RFID tag 14 is interrogated before the capsule 11/12 disperses in the gastrointestinal system, the response of the RFID tag is sufficiently altered or attenuated by the ferrite rings 15/16 to determine that the capsule, tablet or pill has not dispersed in the gastrointestinal system.

The term "alter the antenna characteristics of the RFID tag" means to change the resonate frequency of the antenna and/or to reduce the effective signal strength from the antenna. The specific RFID tag used in the instant invention is not critical. For example, the RFID tag does not have to be a low frequency RFID tag. Of course, the RFID tag should be sufficiently encapsulated or otherwise protected so that it works long enough in the environment of the gastrointestinal system to fulfill its purpose. The RFID tag can be pre-programmed or programmable as is well understood in the art. Any type of RFID tag can be used in the instant invention. The RFID tag is preferably a passive RFID tag powered by the a signal from the RFID reader. However, as described below in greater detail, an active RFID tag (powered, for example, by a battery associated with the RFID tag) can also be used in the instant invention as well as a battery assisted passive RFID tag.

Figure 2:
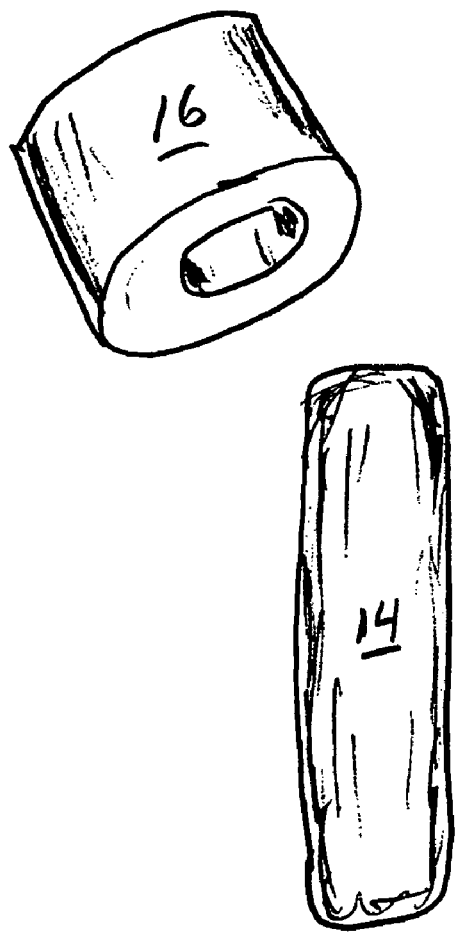
FIG. 2 is an enlarged view of the oral drug delivery system of FIG. 1 after the capsule has dispersed in the gastrointestinal system.
Figure 2:
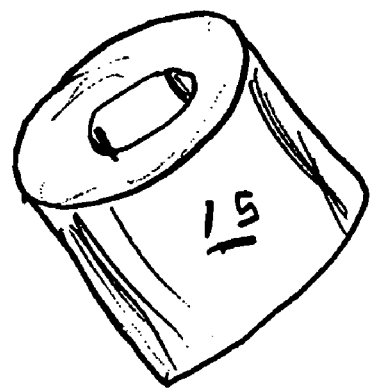

Referring now to FIG. 2, when the oral drug delivery system of FIG. 1 is swallowed the capsule portions disperse in the stomach or intestinal tract thereby allowing the RFID tag 14 to separate from the ferrite rings 15/16 so that the response of the RFID tag 14 is sufficiently detectable to determine that the capsule has dispersed in the gastrointestinal system. It should be understood that capsules useful in the instant invention can be made of materials other than gelatin, such as hydroxypropylmethylcellulose. The capsule of the instant invention can also be made of a material, such as poly (N,N-9-diethylaminoethyl methacrylate), which disperses in an acid environment but not in water.

The specific RFID reader used is not critical in the instant invention. Preferably, the RFID reader system is battery powered and contained in a pouch worn around the waist by a belt. The RFID reader can be programmed to sense and record the type of drug(s) and times of administration thereof for later downloading or preferably for wireless downloading to, for example, healthcare professionals who could even send a reminder signal to the system to remind the patient of his/her noncompliance. Alternatively, an RFID reader system can be incorporated into a watch-like appliance worn on the wrist. Or, an RFID reader system could be clipped to a belt not unlike a cell phone clipped to a belt.

Figure 3:
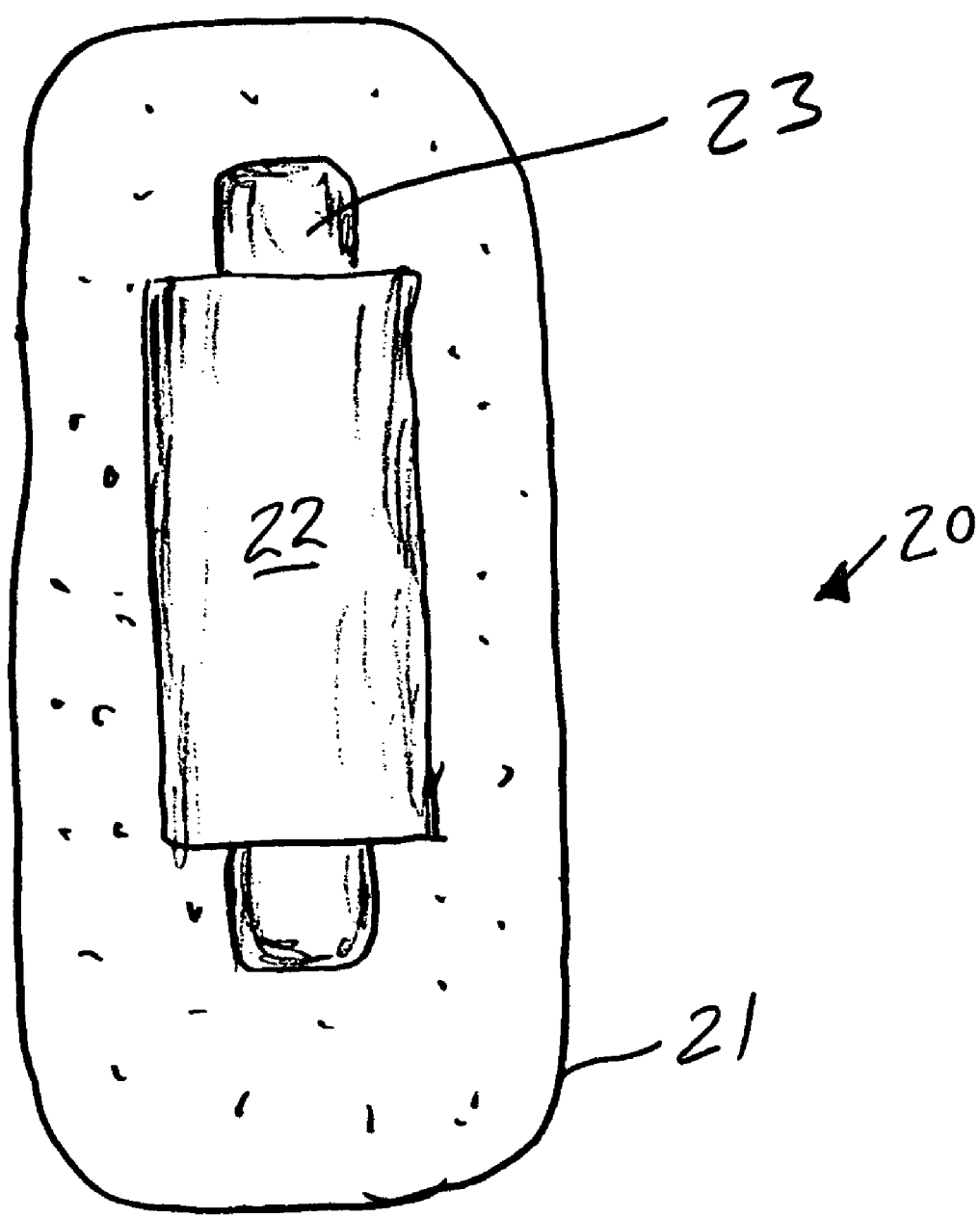
FIG. 3 is an enlarged view, part in cross-section and part in full, of an oral drug delivery system comprising a tablet or pill containing a cylindrical magnet over an RFID tag.

Referring now to FIG. 3, therein is shown an enlarged view, part in cross-section and part in full, of an oral drug delivery system 20 comprising a tablet or pill 21 containing a cylindrical magnet 22 over an RFID tag 23. The magnet 22 alters the antenna characteristics of the RFID tag so that if the RFID tag is interrogated before the tablet or pill 21 disperses in the gastrointestinal system, the response of the RFID tag 23 is sufficiently altered or attenuated to determine that the tablet or pill 21 has not dispersed in the gastrointestinal system and so that if the RFID tag 23 is interrogated after the tablet or pill 21 has dispersed in the gastrointestinal system, the cylindrical magnet 22 separates from the RFID tag 23 so that the response of the RFID tag 23 is sufficiently detectable to determine that the tablet or pill 21 has dispersed in the gastrointestinal system.

Figure 4:
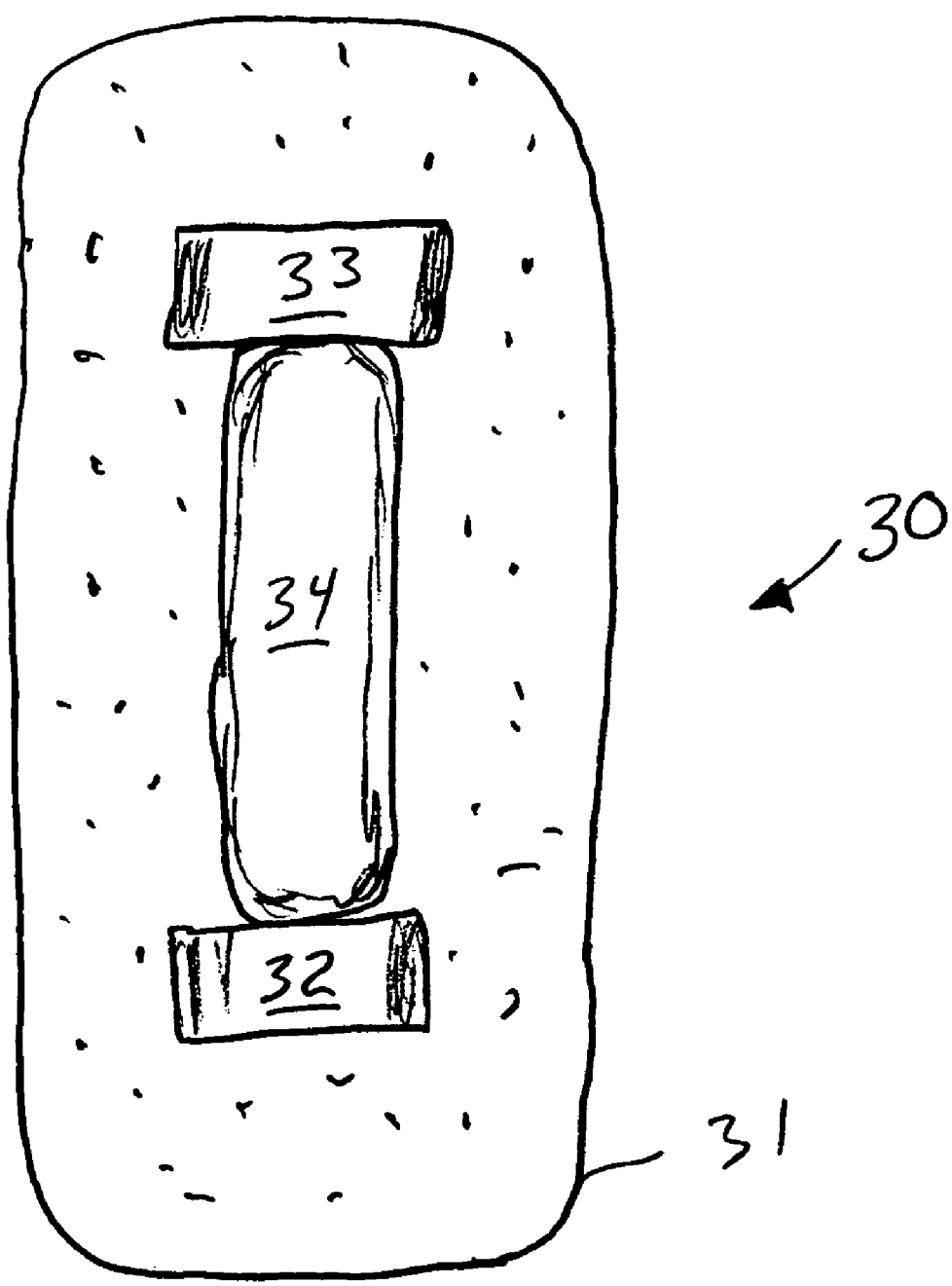
FIG. 4 is an enlarged view, part in cross-section and part in full, of an oral drug delivery system comprising a drug tablet containing pair of ferrite disks positioned at either end of an RFID tag.

Referring now to FIG. 4, therein is shown is an enlarged view, part in cross-section and part in full, of an oral drug delivery system 30 comprising a drug tablet 31 containing a pair of ferrite disks 32/33 positioned at either end of an RFID tag 34. The ferrite disks 32/33 alter the antenna characteristics of the RFID tag 34 so that if the RFID tag 34 is interrogated before the tablet 31 disperses in the gastrointestinal system, the response of the RFID tag 34 is sufficiently altered or attenuated to determine that the tablet 31 has not dispersed in the gastrointestinal system and so that if the RFID tag 34 is interrogated after the tablet 31 has dispersed in the gastrointestinal system, the ferrite disks 32/33 separate from the RFID tag 34 so that the response of the RFID tag 34 is sufficiently detectable to determine that the tablet 31 has dispersed in the gastrointestinal system.

Figure 5:
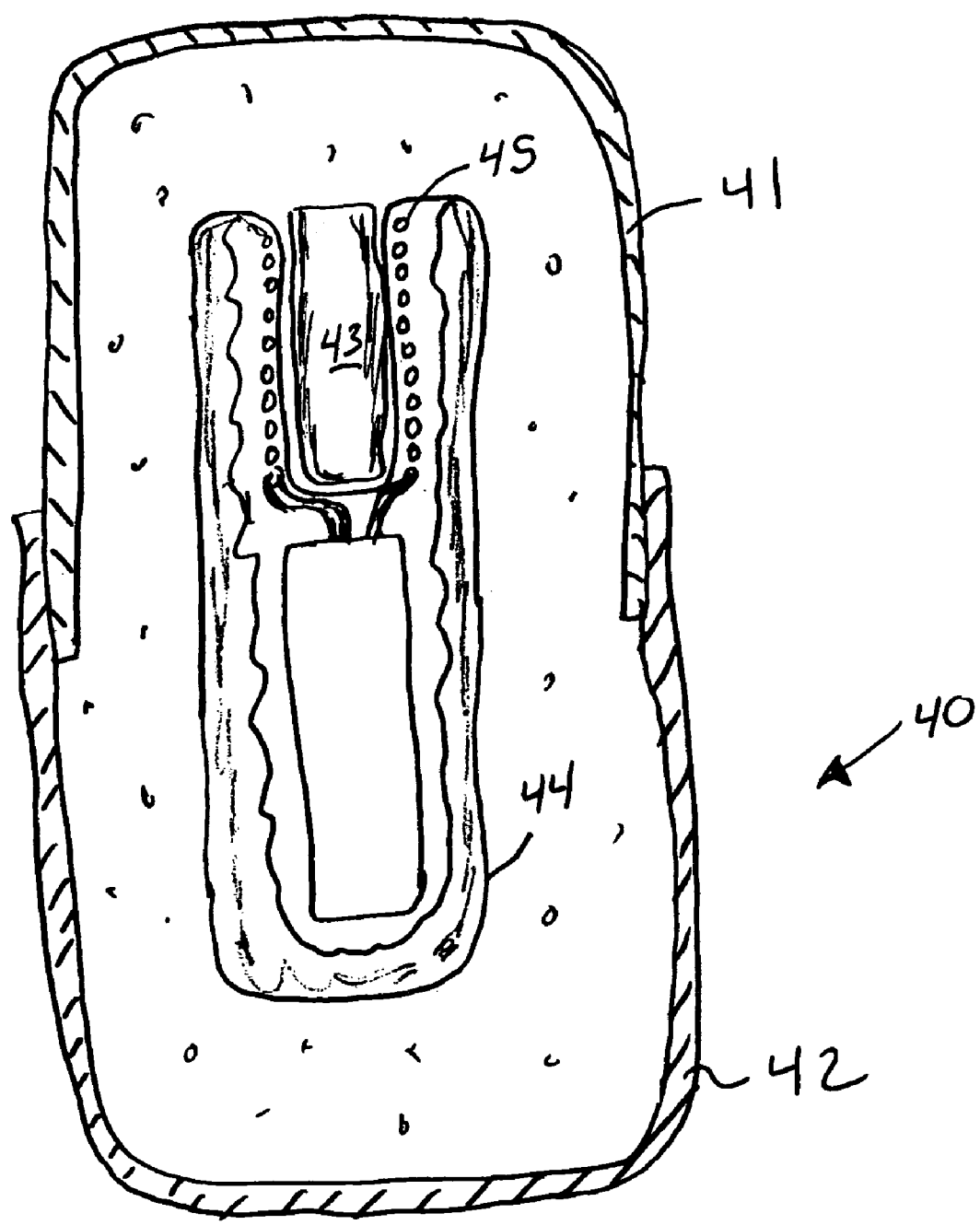
FIG. 5 is an enlarged view part in cross-section, part broken away and part in full, of an oral drug delivery system comprising a capsule containing a magnet positioned in a cavity of an RFID tag adjacent the antenna coil of the RFID tag.

Referring now to FIG. 5, therein is shown an enlarged view part in cross-section, part broken away and part in full, of an oral drug delivery system 40 comprising a capsule 41/42 containing a magnet 43 positioned in a cavity of an RFID tag 44 adjacent the antenna coil 45 of the RFID tag 44. The magnet 43 alters the antenna characteristics of the RFID tag 44 so that if the RFID tag 44 is interrogated before the system 40 disperses in the gastrointestinal system, the response of the RFID tag 44 is sufficiently altered or attenuated to determine that the system 40 has not dispersed in the gastrointestinal system and so that if the RFID tag 44 is interrogated after the system 40 has dispersed in the gastrointestinal system, the magnet 43 separates from the RFID tag 44 so that the response of the RFID tag 44 is sufficiently detectable to determine that the system 40 has dispersed in the gastrointestinal system. Alternatively, the cavity of the RFID tag can, for example and without limitation thereto, be filled with a dispersible ferrite composition that will disperse in the gastrointestinal system when the system 40 is ingested.

Figure 6:
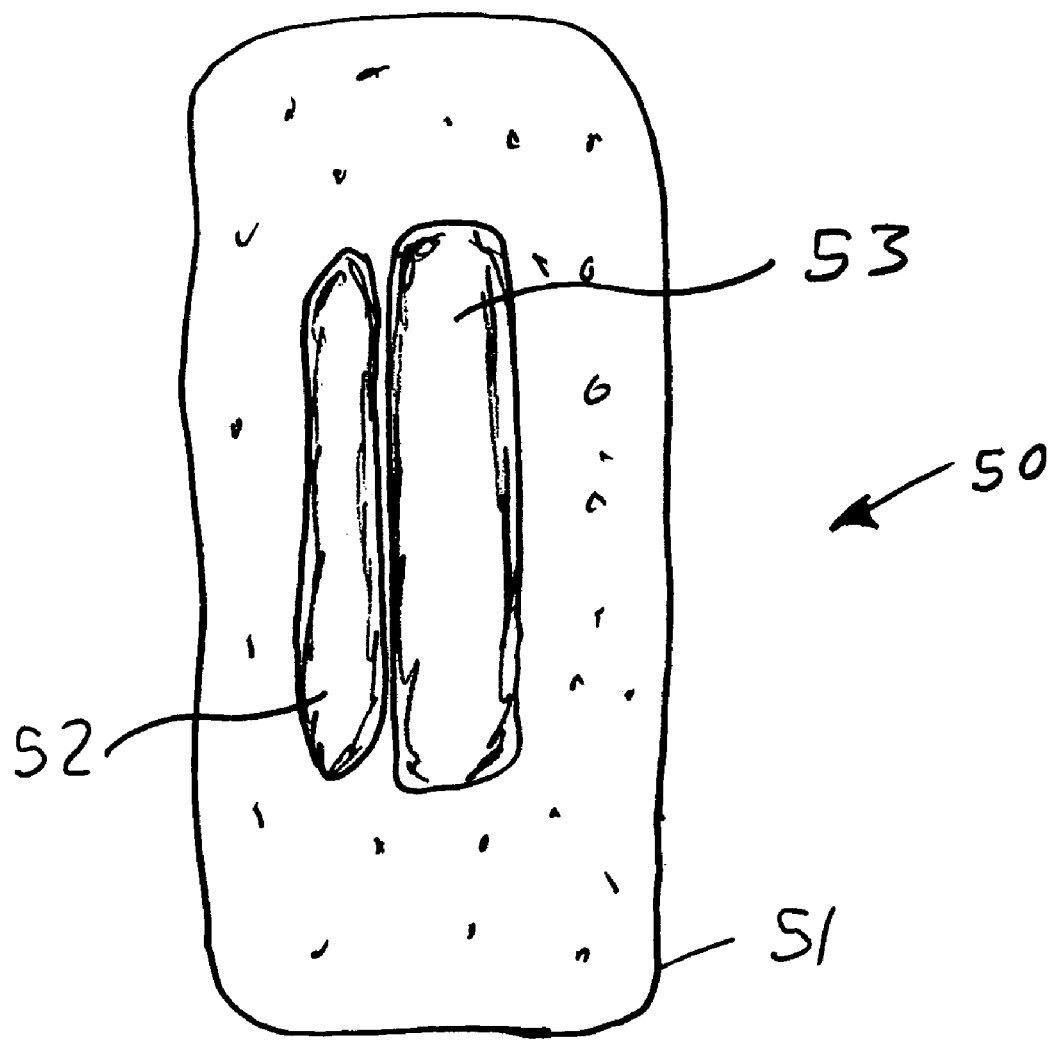
FIG. 6 is an enlarged view, part in cross-section and part in full, of an oral drug delivery system comprising a drug tablet containing an iron rod positioned adjacent an RFID tag.

Referring now to FIG. 6, therein is shown an enlarged view, part in cross-section and part in full, of an oral drug delivery system 50 comprising a drug tablet 51 containing an iron rod 52 positioned adjacent an RFID tag 53. The iron rod 52 alters the antenna characteristics of the RFID tag 53 so that if the RFID tag 53 is interrogated before the system 50 disperses in the gastrointestinal system, the response of the RFID tag 53 is sufficiently altered or attenuated to determine that the system 50 has not dispersed in the gastrointestinal system and so that if the RFID tag 53 is interrogated after the system 50 has dispersed in the gastrointestinal system, the iron rod 52 separates from the RFID tag 53 so that the response of the RFID tag 53 is sufficiently detectable to determine that the system 50 has dispersed in the gastrointestinal system.

Figure 7:
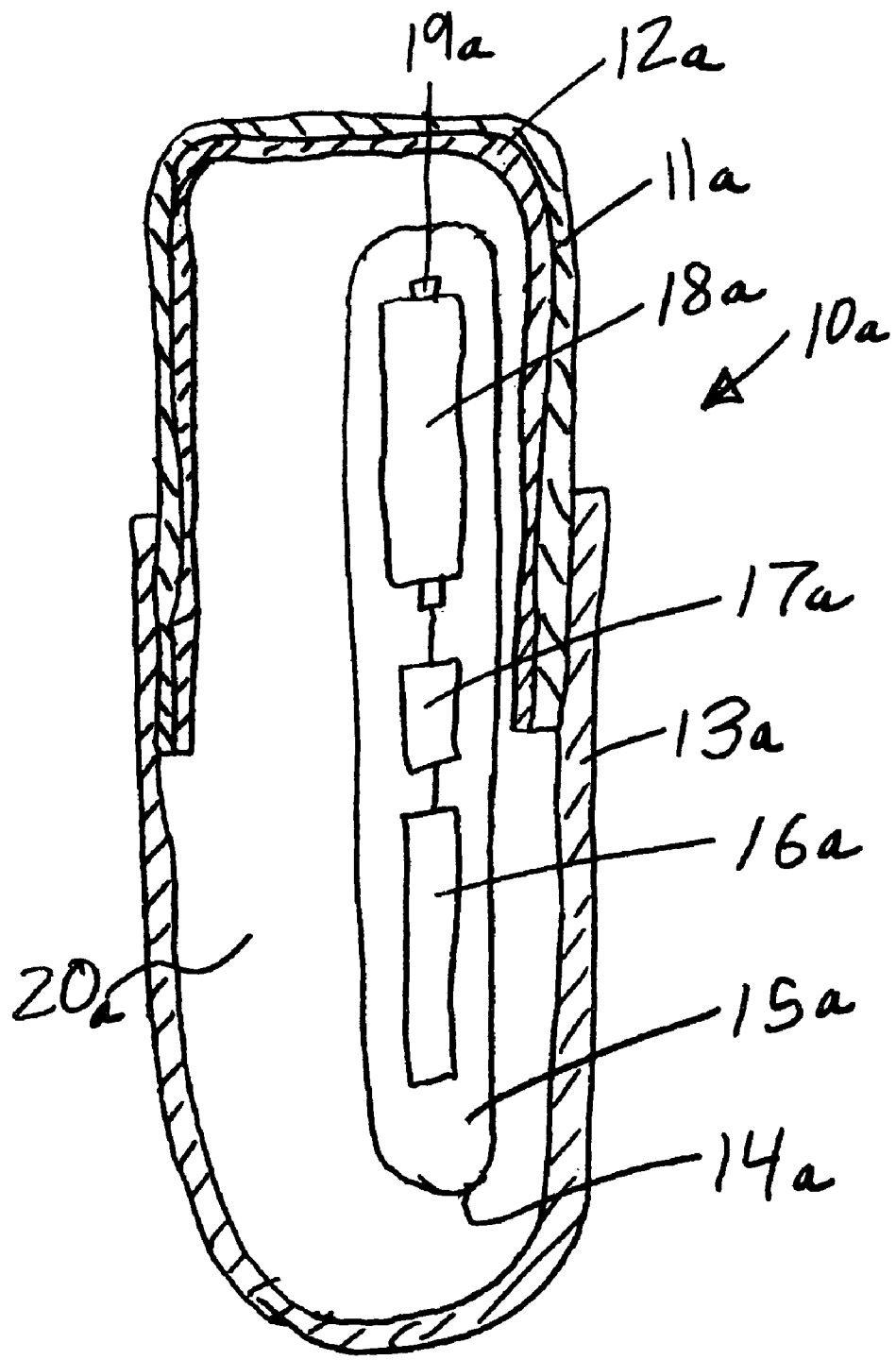
FIG. 7 is an enlarged view, part in cross-section and part in full, of a gelatin capsule containing an RFID tag having an antenna shielded by a cup of gold foil.

Referring now to FIG. 7, therein is shown an oral drug delivery system 10a of the instant invention, comprising an upper gelatin capsule portion 11a and a lower gelatin capsule portion 13a. A Texas Instruments low frequency RFID tag 14a is positioned within the capsule of the system 10a. The tag 14a is encapsulated in glass 15a and includes an RFID chip 16a encoded to identify a drug type, dose, lot number etc. The tag 14a includes a copper coil antenna 18a having a ferrite core 19a in communication with the chip 16a and a capacitor 17a. The remaining volume 20a within the capsule of the system 10a is, of course, available to contain a drug formulation.

The RFID tag can be pre-programmed or programmable as is well understood in the art. The copper coil antenna 18a and ferrite core 19a are a preferred antenna system for the RFID tag 14a of the instant invention because this antenna system is compact even though the wavelength of operation is relatively long. A conventional dipole antenna of the same size as the copper coil antenna 18a requires a relatively short wavelength of operation which can complicate or even frustrate electromagnetic wave communication through human tissue since such short wavelength radiation is easily absorbed or attenuated by water.

A cup of gold foil 12a is positioned inside the upper gelatin capsule portion 11a. When the system 10a is interrogated with an RFID reader (such as the RFID reader available from, for example, Texas Instruments or from the Stoelting Company (Wood Dale, Ill.) it fails to respond because the gold foil 12a shields the antenna 18a. However, when the system 10a is swallowed the capsule portions 11a and 13a disperse in the stomach or intestinal tract thereby freeing the RFID tag 14a from the shielding effect of the gold foil cup 12a so that the RFID tag 14a will now respond to an RFID reader.

The upper gelatin capsule portion 11a is dispersible in the stomach or intestinal tract. However, it is not critical in the embodiment shown in FIG. 7 that the upper capsule portion is so dispersible since the RFID tag will separate from the gold foil 12a as long as the lower capsule portion 13a disperses in the stomach or intestinal tract. Although it is preferable to place the gold foil 12a inside the upper capsule portion 11a as shown in FIG. 1, the gold foil 12a can be placed on the outside of the upper capsule portion 11a. Although gold is the preferred material to shield the antenna 18a of the RFID tag 14a, any metal or other material can be used that is effective to shield the electromagnetic waves and which is approved for ingestion (e.g., iron and nickel are listed by the FDA as Generally Recognized As Safe for ingestion).

It should be understood that capsules useful in the instant invention can be made of materials other than gelatin, such as hydroxypropylmethylcellulose. The capsule of the instant invention can also be made of a material, such as a polymer comprising N,N-9-diethylaminoethyl methacrylate, which disperses in an acid environment but not in water. Similarly, materials such as polymers comprising N,N-9-diethylaminoethyl methacrylate, hydroxypropylmethylcellulose or gelatin can be used instead of gum arabic as a coating material to contain the electromagnetic shielding material.

Figure 8:
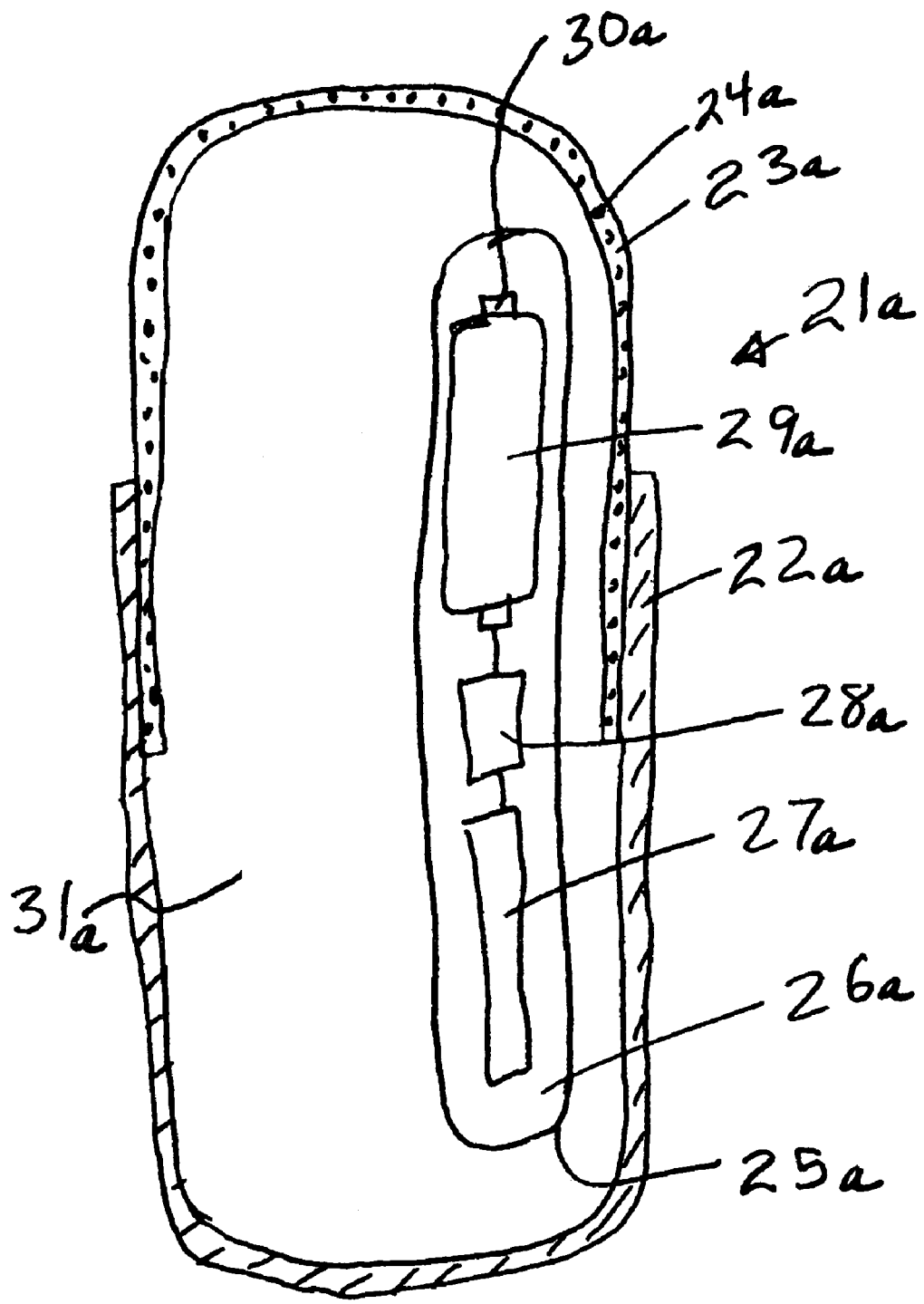
FIG. 8 is an enlarged view, part in cross-section and part in full, of a gelatin capsule containing an RFID tag having an antenna shielded by particles of gold embedded in the gelatin capsule.

Referring now to FIG. 8, therein is shown another oral drug delivery system 21a of the instant invention, comprising an upper gelatin capsule portion 23a and a lower gelatin capsule portion 22a. A Texas Instruments low frequency RFID tag 25a is positioned within the capsule of the system 21a. The tag 25a is encapsulated in glass 26a and includes an RFID chip 27a encoded to identify a drug type, dose, lot number etc. The tag 25a includes a copper coil antenna 29a having a ferrite core 30a in communication with the chip 27a and a capacitor 28a. The remaining volume 31a within the capsule of the system 21a is, of course, available to contain a drug formulation. The upper capsule 23a comprises particles of gold 24a. When the system 21a is interrogated with an RFID reader it fails to respond because the gold particles 24a shield the antenna 29a. However, when the system 21a is swallowed the capsule portions 23a and 22a disperse in the stomach or intestinal tract thereby freeing the RFID tag 25a from the shielding effect of the gold particles 24a so that the RFID tag 25a will now respond to an RFID reader. The lower gelatin capsule portion 22a is dispersible in the stomach or intestinal tract. However, it is not critical in the embodiment shown in FIG. 8 that the lower capsule portion is so dispersible since the RFID tag will separate from the lower capsule portion 22a as long as the upper capsule portion 23a disperses in the stomach or intestinal tract.

Figure 9:
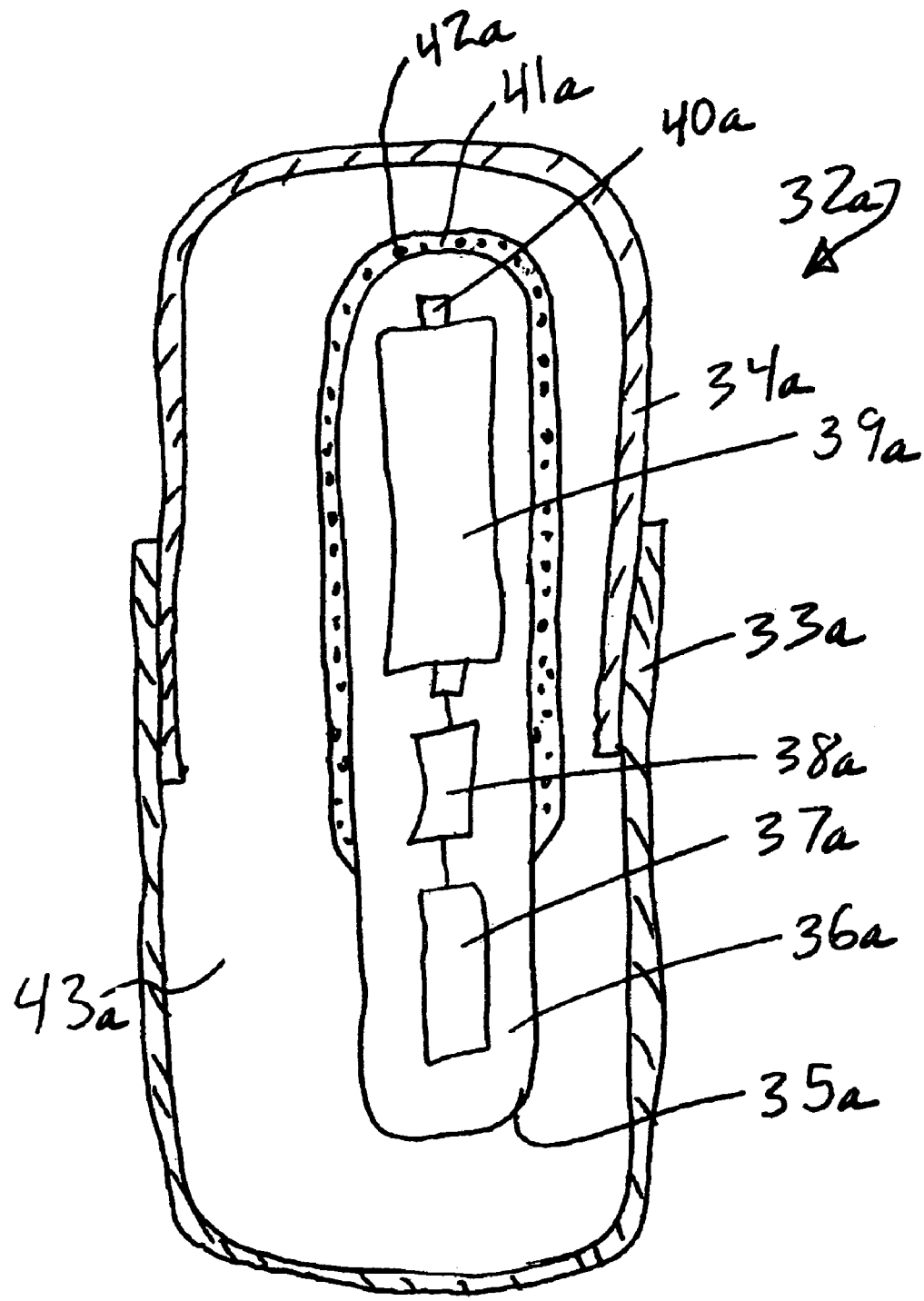
FIG. 9 is an enlarged view, part in cross-section and part in full, of a gelatin capsule containing an RFID tag having an antenna shielded by particles of gold embedded in a gum arabic coating on the RFID tag.

Referring now to FIG. 9, therein is shown another oral drug delivery system 32a of the instant invention, comprising an upper gelatin capsule portion 34a and a lower gelatin capsule portion 33a. A Texas Instruments low frequency RFID tag 35a is positioned within the capsule of the system 32a. The tag 35a is encapsulated in glass 36a and includes an RFID chip 37a encoded to identify a drug type, dose, lot number etc. The tag 35a includes a copper coil antenna 39a having a ferrite core 40a in communication with the chip 37a and a capacitor 38a. The remaining volume 43a within the capsule of the system 32a is, of course, available to contain a drug formulation. The upper end of the RFID tag 35a is coated with a layer of gum arabic 41a containing particles of gold 42a. When the system 32a is interrogated with an RFID reader it fails to respond because the gold particles 42a shield the antenna 39a. However, when the system 32a is swallowed the gum arabic 41a disperses in the stomach or intestinal tract thereby freeing the RFID tag 35a from the shielding effect of the gold particles 42a so that the RFID tag 35a will now respond to an RFID reader.

Figure 10:
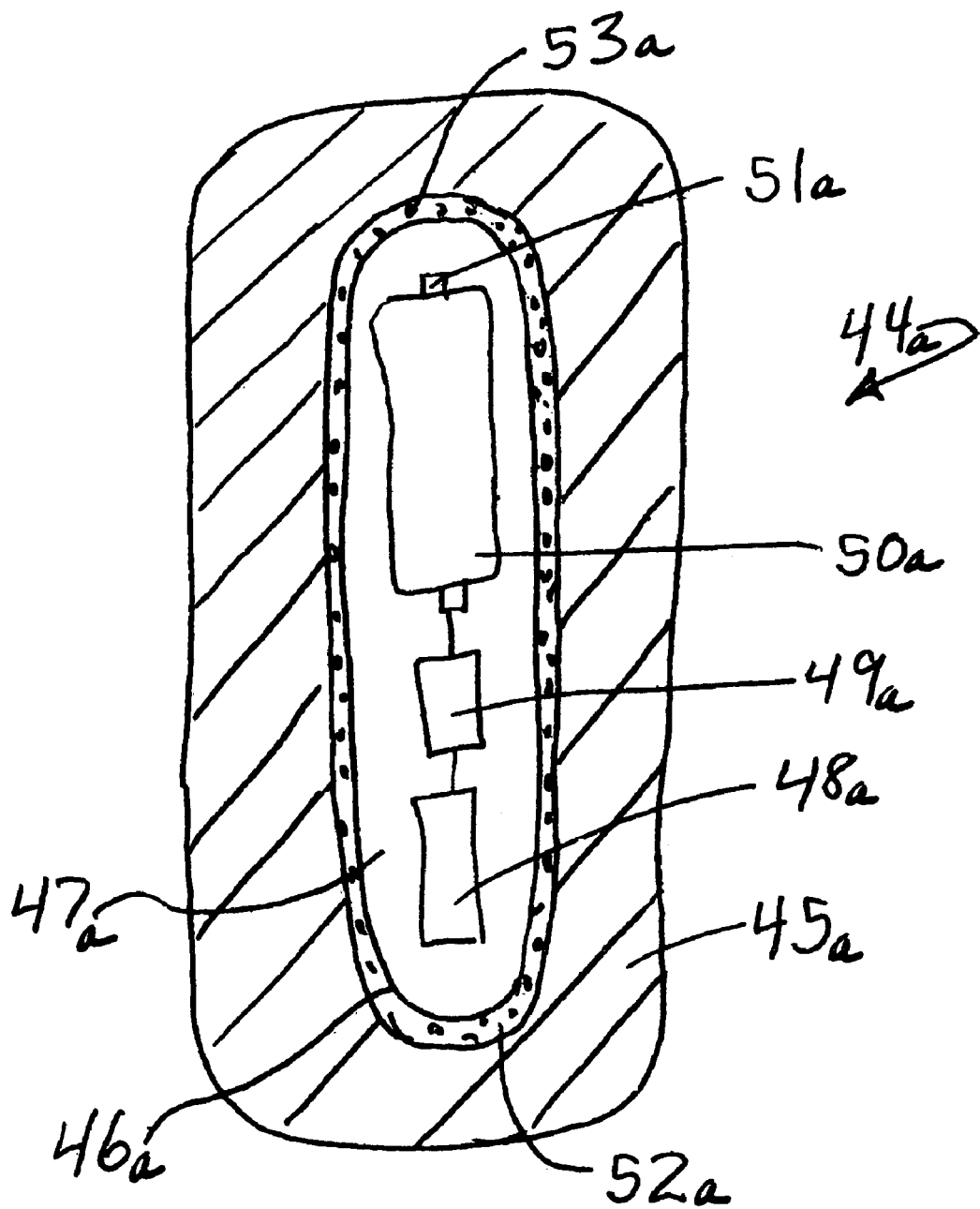
FIG. 10 is an enlarged view, part in cross-section and part in full, of a drug tablet containing an RFID tag having an antenna shielded by particles of gold embedded in a gum arabic coating on the RFID tag.

Referring now to FIG. 10, therein is shown another oral drug delivery system 44a of the instant invention, comprising a tablet or pill 45a containing a drug formulation. A Texas Instruments low frequency RFID tag 46a is positioned within the tablet or pill 45a. The tag 46a is encapsulated in glass 47a and includes an RFID chip 48a encoded to identify a drug type, dose, lot number etc. The tag 46a includes a copper coil antenna 50a having a ferrite core 51a in communication with the chip 48a and a capacitor 49a. The RFID tag 46a is coated with a layer of gum arabic 52a containing particles of gold 53a. When the system 44a is interrogated with an RFID reader it fails to respond because the gold particles 53a shield the antenna 50a. However, when the system 44a is swallowed the tablet or pill 45a as well as the gum arabic 52a disperses in the stomach or intestinal tract thereby freeing the RFID tag 46a from the shielding effect of the gold particles 53a so that the RFID tag 46a will now respond to an RFID reader. It should be understood that the layer of gum arabic 52a containing the gold particles 53a can also positioned on the surface of the tablet or pill 45a.

In another embodiment, the instant invention is an oral drug delivery device, comprising: (a) a drug tablet, pill or capsule designed to disperse in the gastrointestinal system; (b) an RFID tag positioned in the tablet, pill or capsule, the RFID tag comprising a switch, the switch turning on or off in response to conditions in the gastrointestinal system so that if the RFID tag is interrogated before the tablet, pill or capsule disperses in the gastrointestinal system, the response of the RFID tag signifies that the capsule has not dispersed in the gastrointestinal system and so that if the RFID tag is interrogated after the tablet, pill or capsule disperses in the gastrointestinal system, the response of the RFID tag signifies that the tablet, pill or capsule has dispersed in the gastrointestinal system. If the RFID tag is an active RFID tag, then the switch preferably turns on the RFID tag after the tablet, pill or capsule has dispersed in the gastrointestinal system (and thus the term "interrogate" throughout the instant invention includes reading the signal from such an active RFID tag). Alternatively, and without limitation thereto, the switch can be used to change a logic function of the RFID tag.

Figure 11:
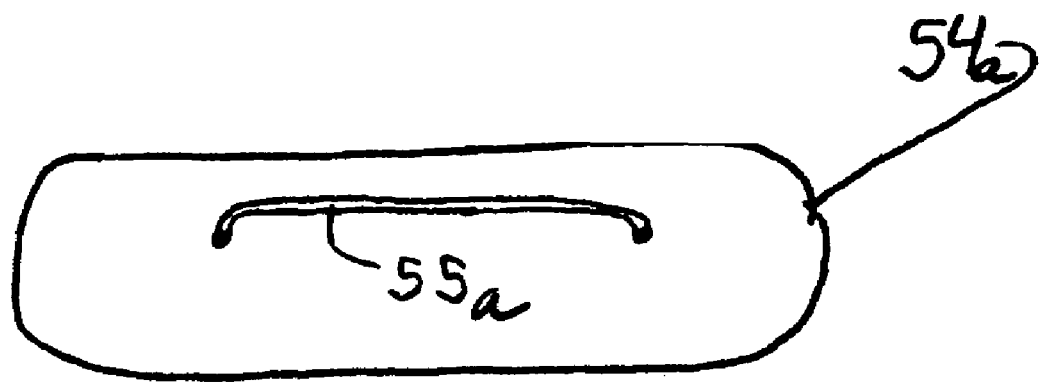
FIG. 11 is an enlarged view of an RFID tag having an external fine iron wire shorting the antenna of the RFID tag.
Figure 12:
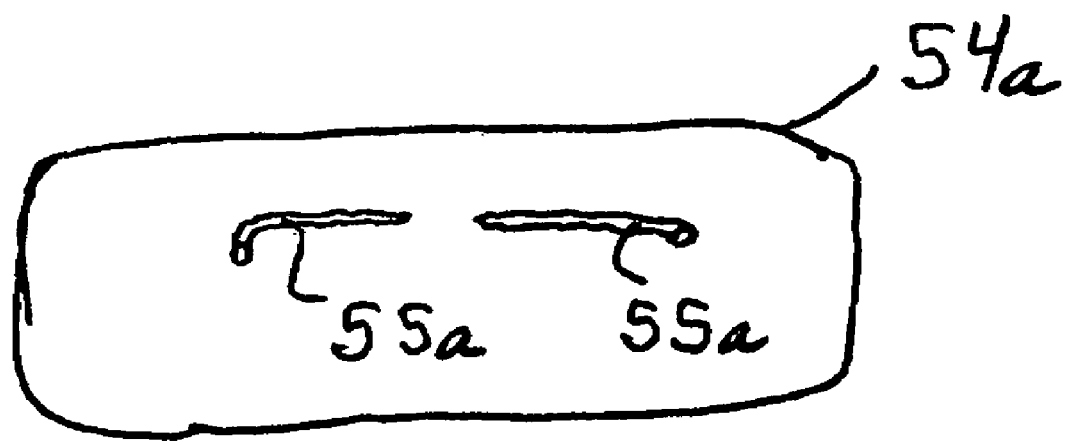
FIG. 12 is an enlarged view of the RFID tag of FIG. 11 after the RFID tag has been exposed to gastric juices for ten minutes to corrode and sever the fine iron wire.

Referring now to FIG. 11, therein is shown an RFID tag 54a having a thin iron wire 55a projecting therefrom. The iron wire 55a serves as a "switch" for the RFID tag, turning the RFID tag off or preferably on when the iron wire 55a is severed. For example, the iron wire 55a can be positioned to short the antenna of the RFID tag 54a so that when the iron wire 55a is severed, the RFID tag 54a will respond to an RFID reader. Referring now to FIG. 12, therein is shown the RFID tag 54a of FIG. 11 after the RFID tag 54a has been exposed to the acidic conditions of the stomach. The thin iron wire 55a has been severed by corrosion. The RFID tag of FIG. 11 can thus be placed in a drug capsule or processed in a drug tablet or pill so that when the capsule, tablet or pill is ingested, the RFID tag will then respond to an RFID reader. It should be understood that other materials can be used in place of the iron wire 55a such as an electrically conductive material that disperses upon exposure in the gastrointestinal system such as a layer of a polymer comprising N,N-9-diethylaminoethyl methacrylate containing a relatively high concentration of gold particles printed on the capsule or tablet so that before its dispersion in the gastrointestinal system, the layer is electrically conductive.

Figure 13:
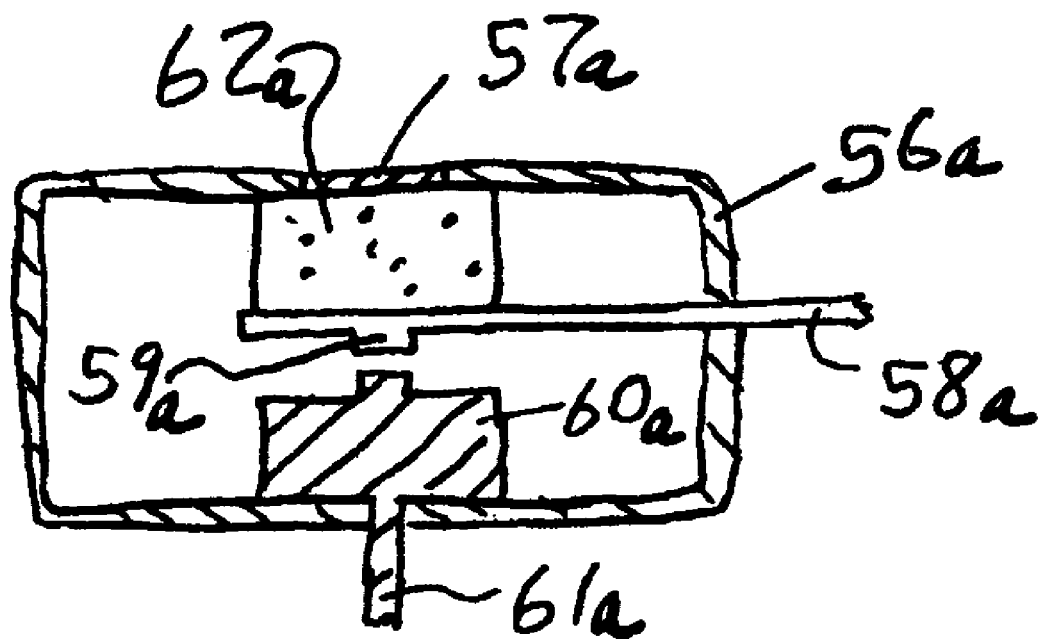
FIG. 13 is an enlarged side view, part in cross-section and part in full, of a switch which turns on if exposed to gastric juices.
Figure 14:
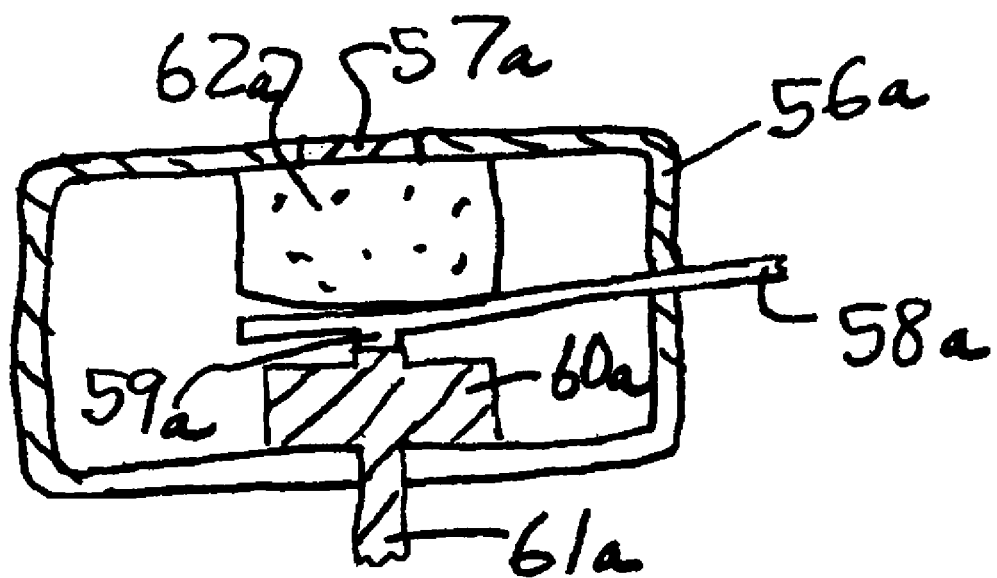
FIG. 14 is an enlarged side view, part in cross-section and part in full, of the switch of FIG. 13 after exposure to gastric juices.

Referring now to FIG. 13, therein is shown a switch system for an RFID tag (not shown) for turning the RFID tag on when the contacts of the switch are closed. The switch system of FIG. 13 includes a small case 56a having a water permeable disk 57a and a water swellable gel 62a. An upper contact 59a is connected to a first electrical lead 58a extending from the case 56a. A lower contact 60a is connected to a second electrical lead 61a extending from the bottom of the case 56a. Referring now to FIG. 14, when the switch system is exposed to water (for example after ingestion into the stomach) the water swellable gel 62a swells and pushes upper contact 59a into electrical contact with lower contact 60a, thereby closing the switch to turn off or, preferably, turn on (or off) the RFID tag. Such an RFID tag can be placed in a drug capsule or processed in a drug tablet or pill so that when the capsule, tablet or pill is ingested, the RFID tag will then respond (or stop responding) to an RFID reader.

Figure 15:
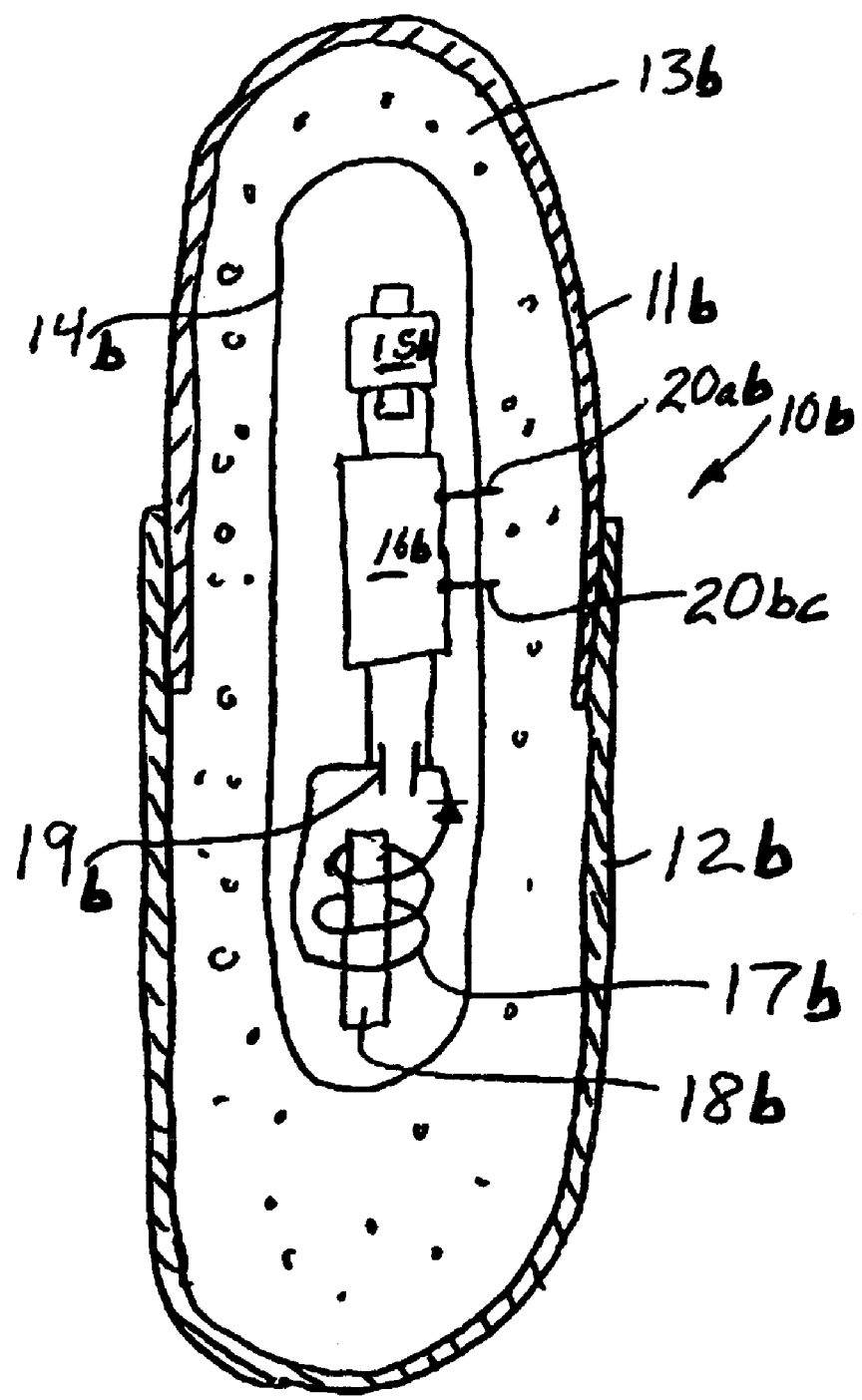
FIG. 15 is an enlarged view, part in cross-section and part in full, of a gelatin capsule containing an active RFID tag powered by a kinetic generator and incorporating a conductivity switch.

Referring now to FIG. 15, therein is shown an enlarged view, part in cross-section and part in full, of one oral drug delivery system embodiment 10b of the instant invention including an upper gelatin capsule portion 11b and a lower gelatin capsule portion 12b. The gelatin capsule 11b/12b contains a drug formulation 13b and an active encapsulated RFID tag 14b powered by a kinetic generator and incorporating a conductivity detector. The kinetic generator is comprised of a magnet 18b suspended in a coil 17b. The capacitor 19b provides power to RFID circuitry 16b. When the oral drug delivery system 10b enters the gastrointestinal system, the gelatin capsule 11b/12b, drug formulation 13b and active RFID tag 14b are dispersed into the electrolyte solution of the gastrointestinal system and movement of the magnet 18b in the coil 17b charges capacitor 19b to power the RFID circuitry 16b. Electrodes 20ab and 20bc of a conductivity detector system activate the RFID circuitry 16b when the conductivity detector system senses the conductivity of the electrolyte solution of the gastrointestinal system. RFID circuitry 16b is connected to antenna 15b (shown as a copper coil would on a ferrite core) which transmits a signal preferably coded to identify the drug formulation, dose and lot number. Alternatively (and preferably) the kinetic generator system is replaced by a battery.

Figure 16:
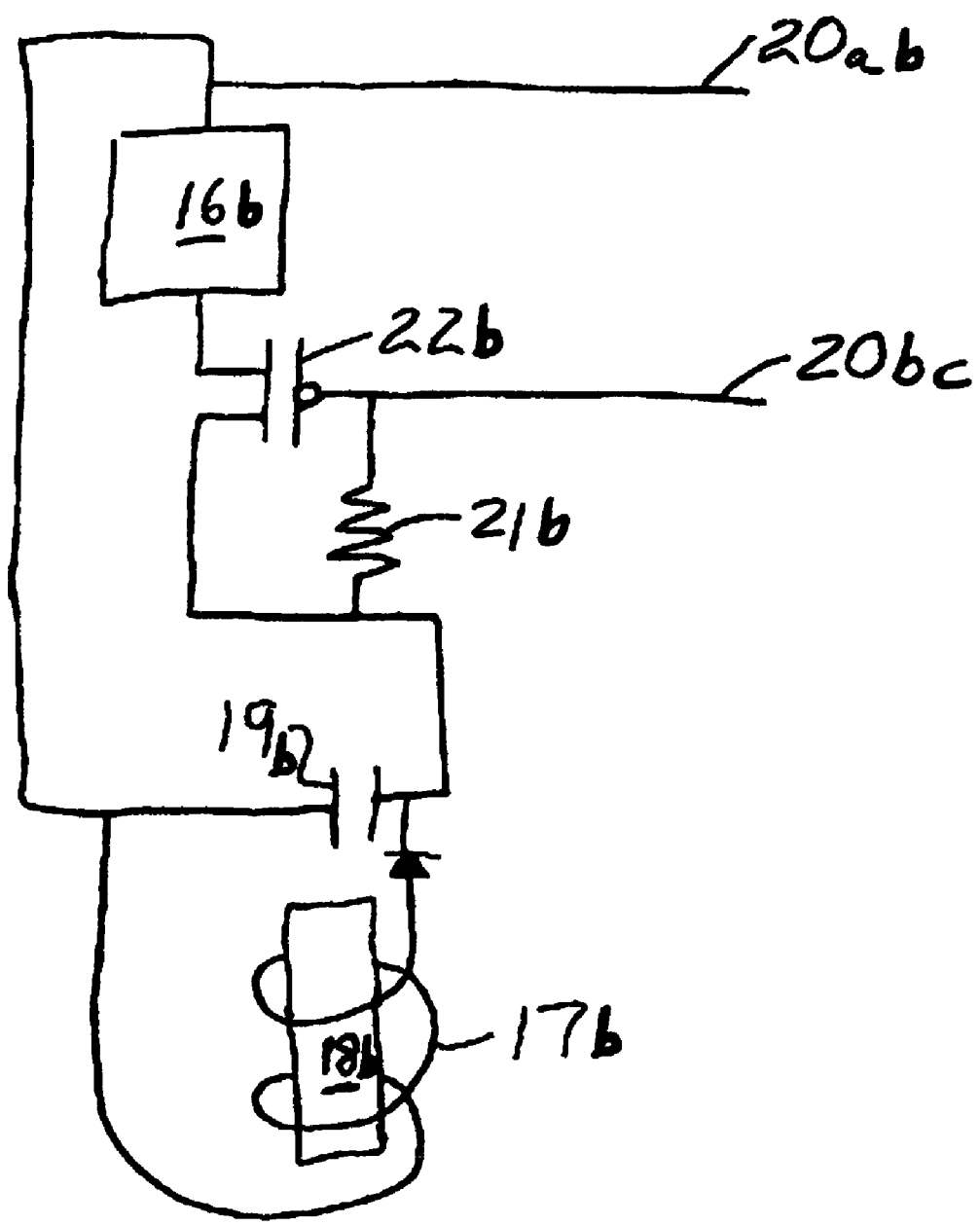
FIG. 16 is a schematic drawing showing the conductivity switch of FIG. 15 in greater detail.

Referring now to FIG. 16, therein is shown a schematic drawing of the conductivity detector of FIG. 15 in greater detail. A p-FET transistor 22b and bias resistor 21b are incorporated to activate the RFID circuitry 16b from capacitor 19b when the conductivity of the electrolyte solution of the gastrointestinal system is detected by way of the electrodes 20ab and 20bg. Additionally, the p-FET circuit could be replaced by an n-FET, CMOS gate, or other electronic circuits using electronic design methods well known in the art.

Figure 17:
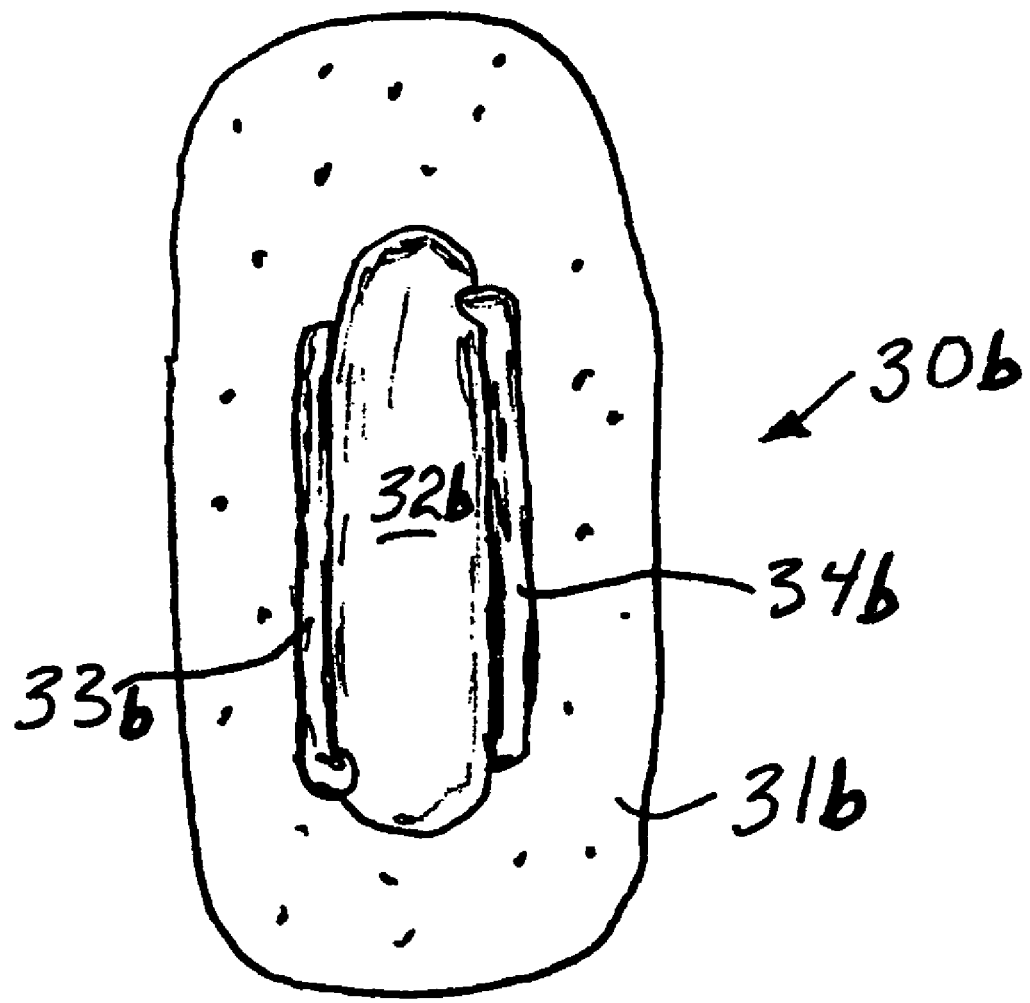
FIG. 17 is an enlarged view, part in cross-section and part in full, of a drug tablet containing an active RFID tag powered by a battery activated by the action of the electrolyte of the gastrointestinal system in contact with the anode and cathode of the battery.

Referring now to FIG. 17, therein is shown is an enlarged view, part in cross-section and part in full, of a drug tablet 30b containing a drug formulation 31b and an active RFID tag 32b powered by a battery activated by the action of the electrolyte solution of the gastrointestinal system in contact with the copper anode 33b and zinc cathode 34b of the battery. In this embodiment the switch and the RFID power source are unified, i.e., when the RFID tag of tablet 30b is dispersed in the gastrointestinal system, the electrolyte solution thereof generates the electrical power for the RFID tag 32b by way of the copper anode 33b and zinc cathode 34b. The use of copper in the anode and zinc in the cathode of this embodiment are not critical in the instant invention, i.e., any suitable pair of materials can be used such as carbon and zinc or silver and zinc.

Figure 18:
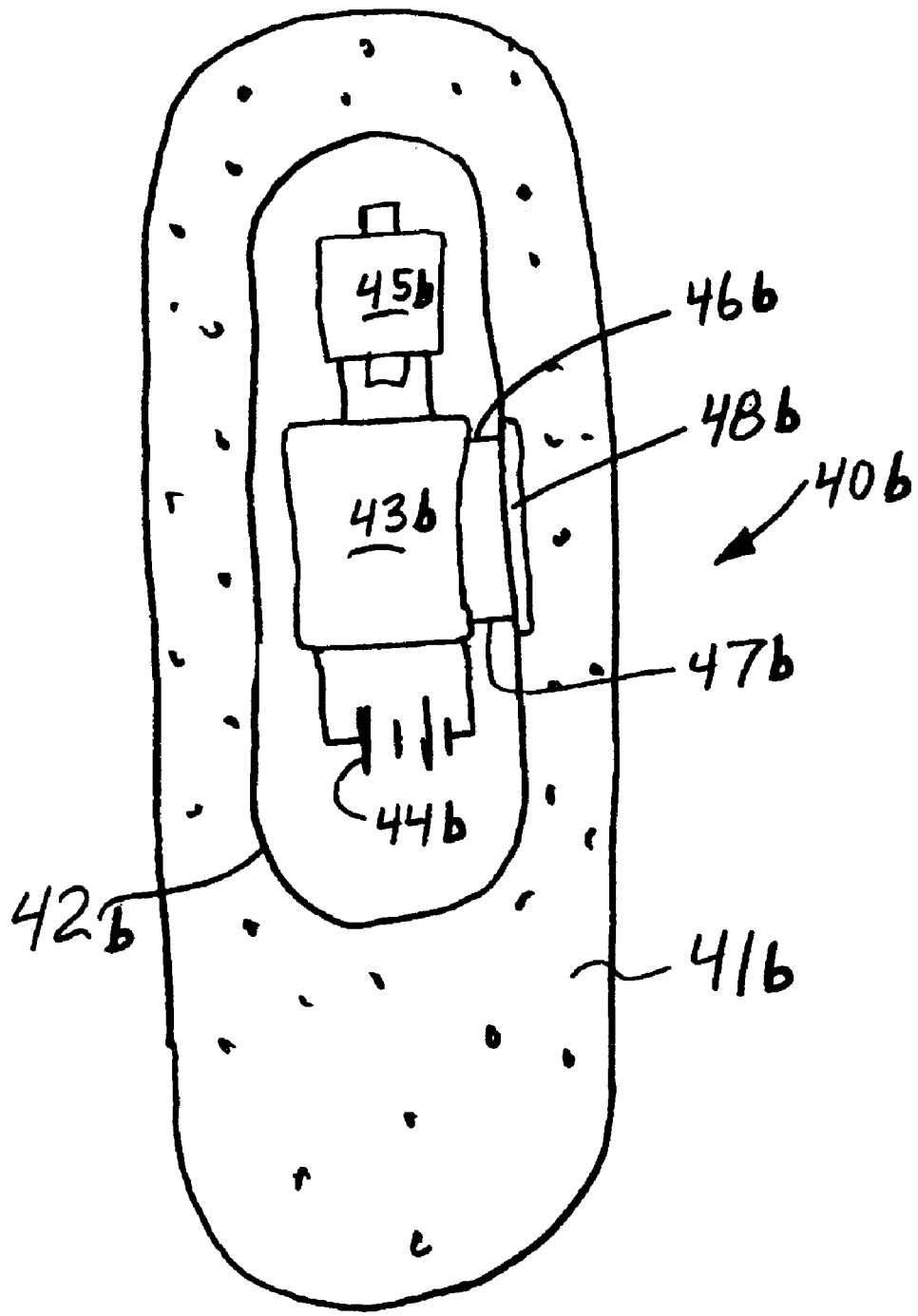
FIG. 18 is an enlarged view, part in cross-section and part in full, of a drug tablet containing an active RFID tag and a dissolving link switch.

Referring now to FIG. 18, therein is shown an enlarged view, part in cross-section and part in full, of a drug tablet 40b containing drug formulation 41b and an active RFID tag 42b containing RFID circuitry 43b connected to antenna system 45b. The RFID circuitry 43b is powered by battery 44b. An electrically conducting layer of powdered silver, carbon, or other conductive material in gelatin 48b provides electrical conduction between electrodes 46b and 47b such that when the tablet 40b disperses in the gastrointestinal tract, the electrolyte solution thereof dissolves the gelatin 48b and alters the electrical conductivity between electrodes 46b and 47b thereby activating RFID circuitry 43b.

Figure 19:
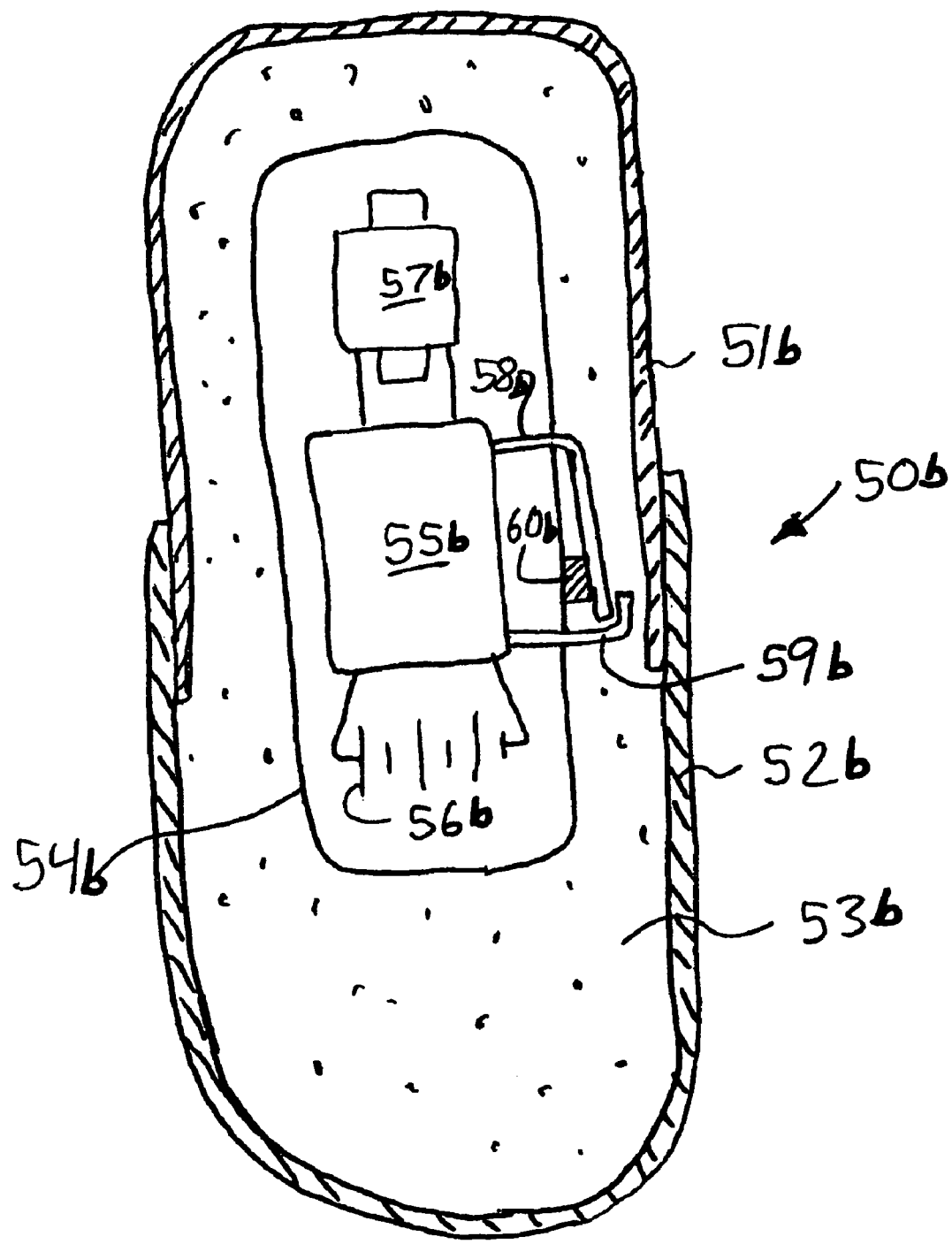
FIG. 19 is an enlarged view, part in cross-section and part in full, of a drug capsule containing an active RFID tag and a switch based sensor.

Referring now to FIG. 19, therein is shown an enlarged view, part in cross-section and part in full, of one oral drug delivery system embodiment 50b of the instant invention including an upper gelatin capsule portion 51b and a lower gelatin capsule portion 52b. The gelatin capsule 51b/52b contains a drug formulation 53b and an active encapsulated RFID tag 54b containing RFID circuitry 55b connected to antenna system 57b. The RFID circuitry 55b is powered by battery 56b. A pad of water swellable polymer 60b is positioned so that when the oral drug delivery system 50b is dispersed in the gastrointestinal system, the electrolyte solution thereof swells the water swellable polymer 60b causing electrical conductor 58b to contact electrical conductor 59b altering the electrical conductivity between the conductors 58b and 59b thereby activating RFID circuitry 55b. It should be understood that the swelling of the water swellable polymer 60b could easily be arranged to open a switch rather than closing a switch. For example, the swelling of a water swellable polymer could easily be arranged to open a switch of the type shown in FIG. 19 or to break a thin wire. Alternatively, the space between conductors 58b and 59b could be filled with a soluble material that would dissolve in the gastrointestinal system allowing the conductors to touch and close the switch. Alternatively, a pressure switch could be used to sense the increased pressure when the active RFID tag of the instant invention was dispersed in the gastrointestinal tract.

Figure 20:
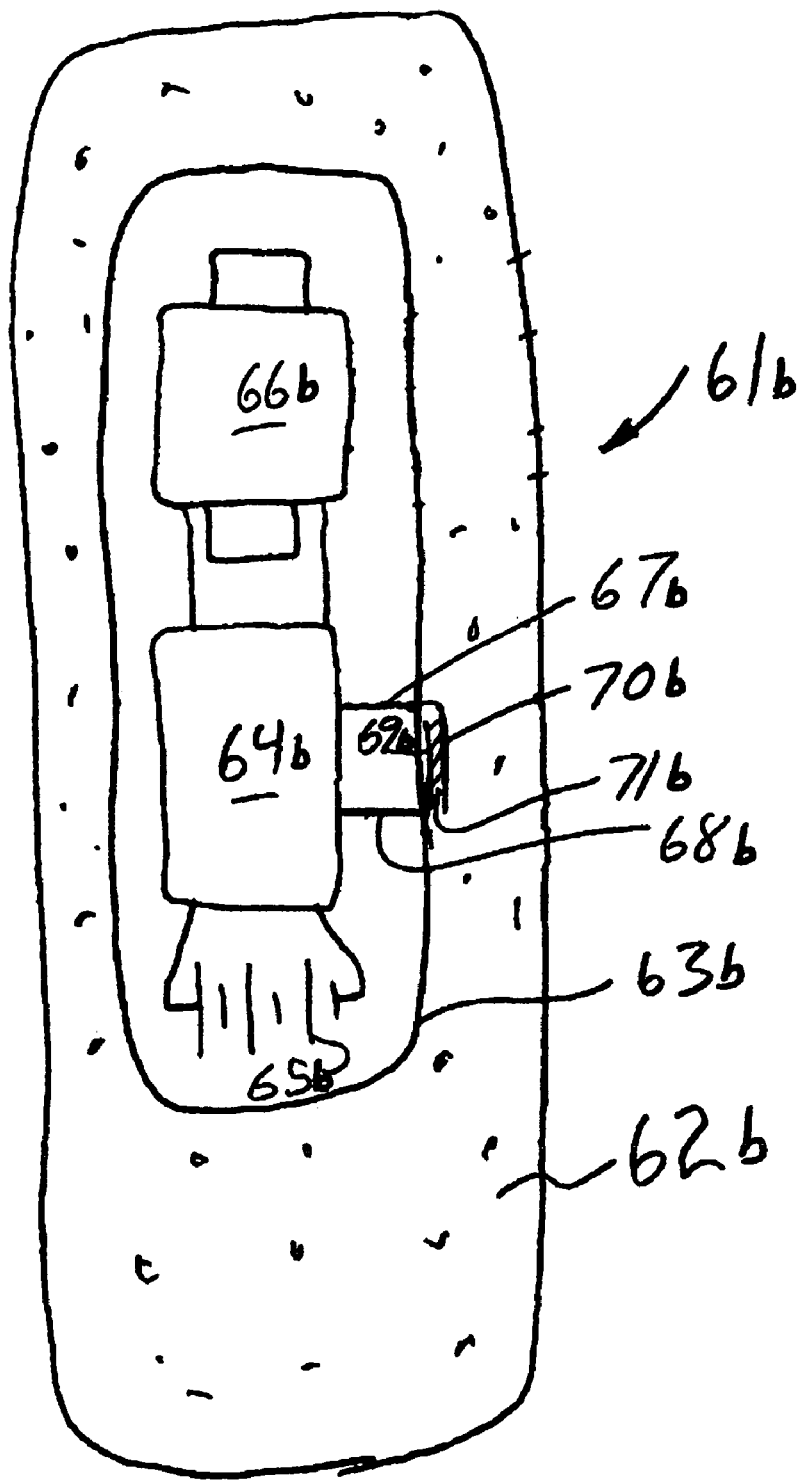
FIG. 20 is an enlarged view, part in cross-section and part in full, of a drug tablet containing an active RFID tag and a capacitor based switch.

Referring now to FIG. 20 therein is shown an enlarged view, part in cross-section and part in full, of one oral drug delivery tablet 61b of the instant invention. The tablet 61b contains a drug formulation 62b and an active encapsulated RFID tag 63b containing RFID circuitry 64b connected to antenna system 66b. The RFID circuitry 64b is powered by battery 65b. A film of water swellable polymer 68b is positioned between first capacitor plate 69b and second capacitor plate 70b so that when the oral drug delivery system 61b is dispersed in the gastrointestinal tract, the electrolyte solution thereof swells the water swellable polymer 70b altering the capacitance between plates 69b and 70b thereby activating RFID circuitry 55b via electrical conductors 67b and 68b. Alternatively the capacitor plates 69b and 70b could comprise conductive wires or pads placed near the surface of 63b such that the dielectric constant of the surroundings would change with ingestion (from air to gastrointestinal electrolyte) altering the capacitance thereby activating the RFID circuitry.

Figure 21:
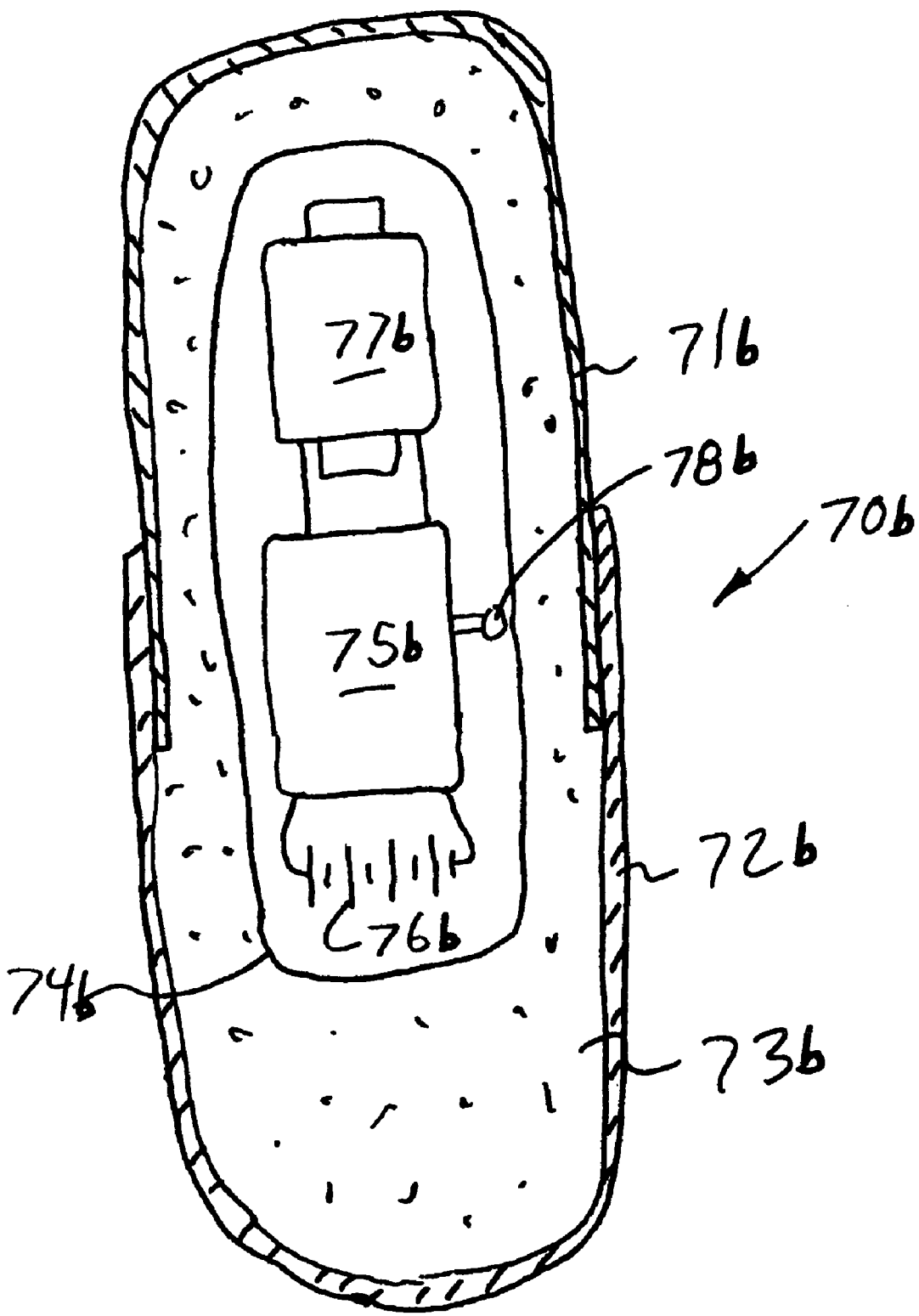
FIG. 21 is an enlarged view, part in cross-section and part in full, of a drug capsule containing an active RFID tag and a temperature based switch.

Referring now to FIG. 21, therein is shown an enlarged view, part in cross-section and part in full, of one oral drug delivery system embodiment 70b of the instant invention including an upper gelatin capsule portion 71b and a lower gelatin capsule portion 72b. The gelatin capsule 71b/72b contains a drug formulation 73b and an active encapsulated RFID tag 74b containing RFID circuitry 75b connected to antenna system 77b. The RFID circuitry 75b is powered by battery 76b. A thermistor 78b is in electrical communication with RFID circuitry 75b so that when the oral drug delivery system 70b is dispersed in the gastrointestinal tract the RFID circuitry 75b can sense the change in temperature thereby and begin sending (or altering) its signal via the antenna system 77b. The RFID circuitry 75b is preferably programmed to differentiate between the temperature profile with time that occurs when a patient swallows the oral drug delivery system 70b versus placing the oral drug delivery system 70b in, for example, a glass of hot water. Alternatively, a temperature sensitive switch can be used instead of the thermistor 78b.

In another embodiment, the instant invention is an oral drug delivery device, comprising: (a) a capsule, tablet or pill designed to disperse in the gastrointestinal system; (b) a first non-anti-collision RFID tag positioned in the capsule; (c) a second non-anti-collision RFID tag positioned in the capsule, so that if the RFID tags are interrogated by an RFID reader before the capsule, tablet or pill disperses in the gastrointestinal system, the response of the RFID tags collide and so that after the dispersible material of the capsule has dispersed in the gastrointestinal system thereby allowing the first and second non-anti-collision tags to separate from each other, then the response of the RFID tags is sufficiently different from each other to determine that the capsule has dispersed in the gastrointestinal system.

Figure 22:
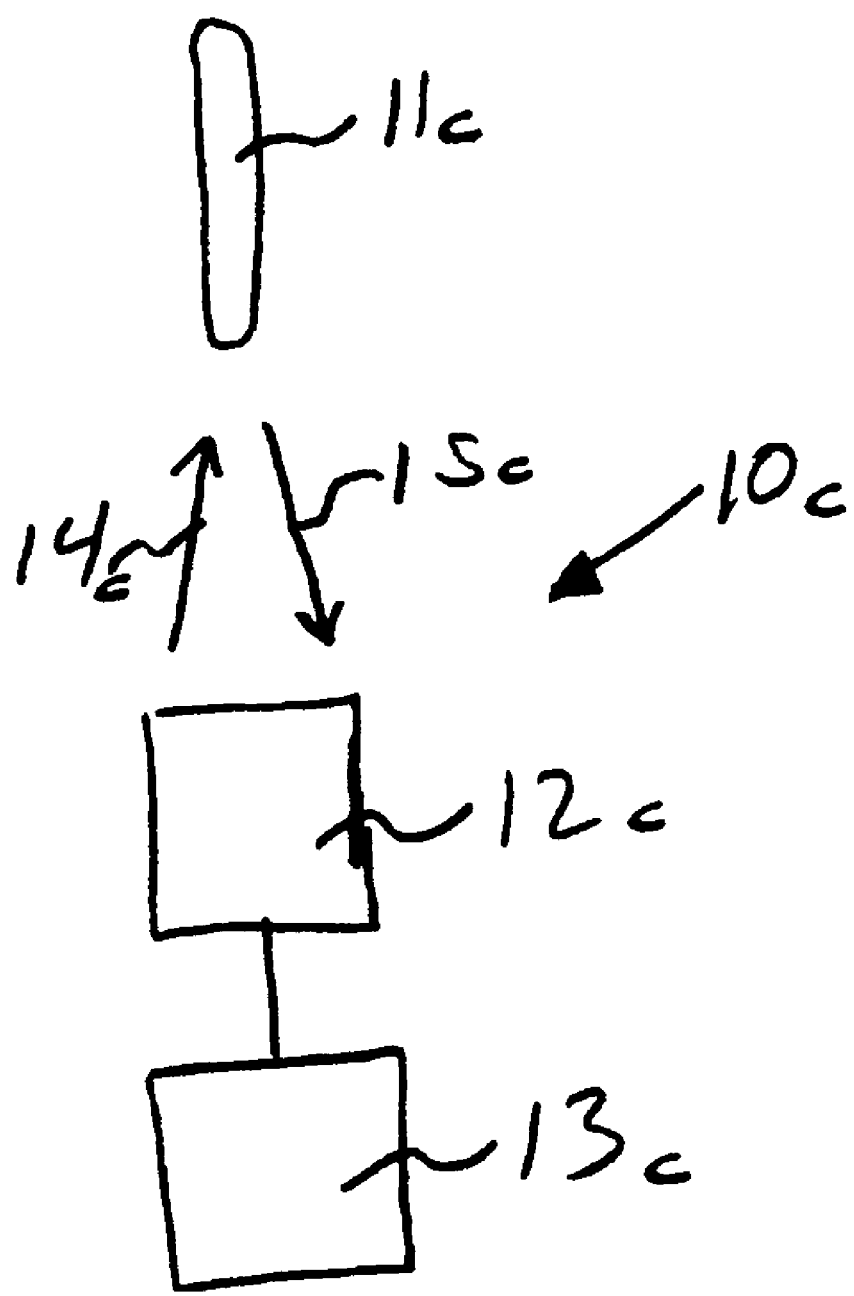
FIG. 22 is a schematic view of a typical prior art RFID system including a passive RFID tag and an RFID reader or interrogator.

Referring now to FIG. 22, therein is shown a schematic view of a typical RFID system 10c including a passive RFID tag 11c and an RFID reader or interrogator 12c which is usually associated with a host computer or microprocessor system 13c for data storage and manipulation. The RFID reader or interrogator 12c transmits a radio frequency energizing/command signal 14c which is received by the RFID tag 11c to produce a return data signal 15c to be received by the reader 12c.

Figure 23:
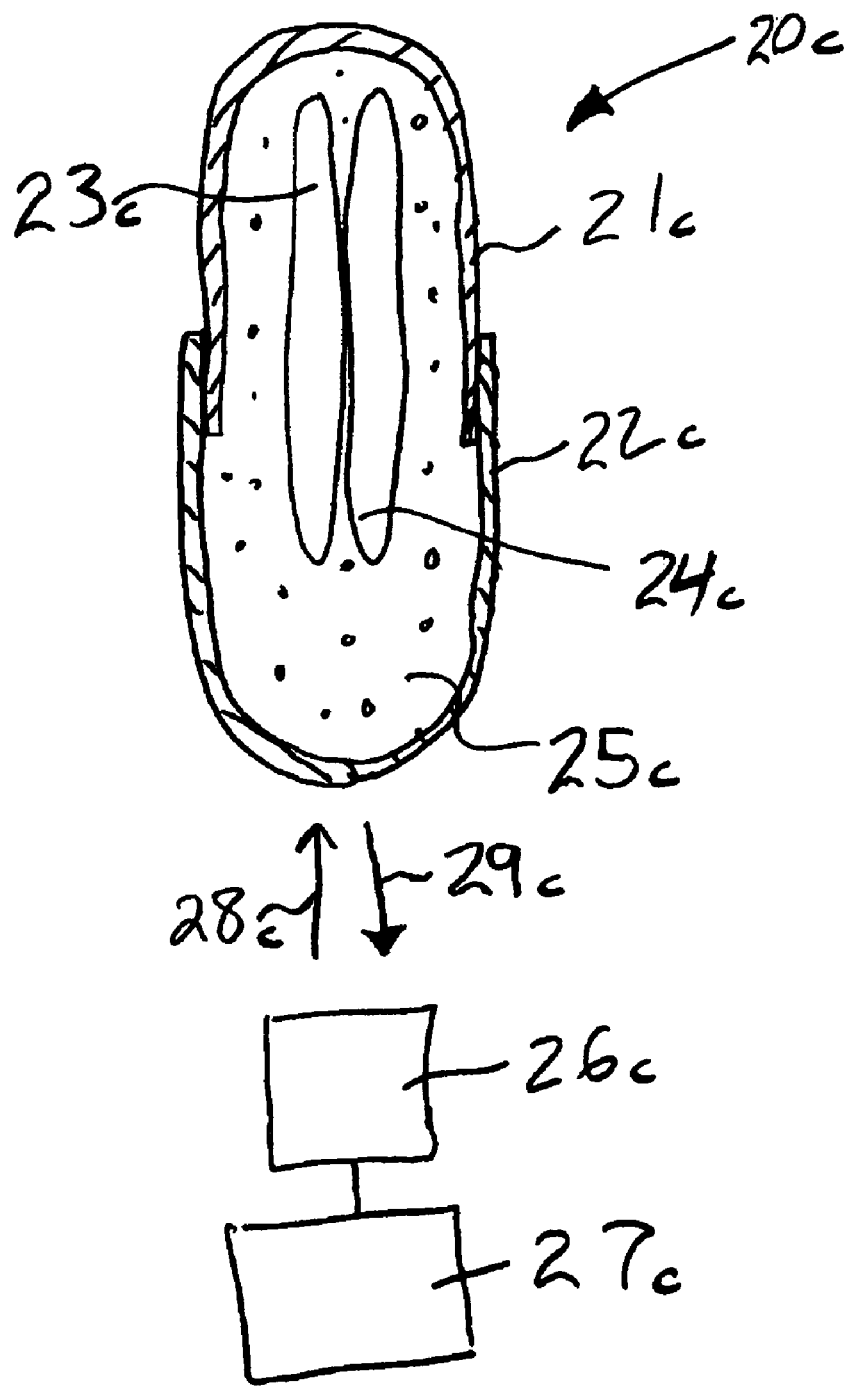
FIG. 23 shows a cross-sectional view of a gelatin capsule containing a pair of passive non-anti-collision RFID tags being interrogated by an RFID reader.

Referring now to FIG. 23, therein is shown shows a cross-sectional view of a gelatin capsule 21c/22c containing a drug formulation 25c, a first non-anti-collision passive RFID tag 23c, a second non-anti-collision passive RFID tag 24c, so that if the RFID tags 23c and 24c are interrogated by energizing/command signal 28c from an RFID reader 26c before the capsule 21c/22c disperses in the gastrointestinal system, the response data signals 29c of the RFID tags 23c/24c "collide". An active RFID tag is an RFID tag having its own power source, usually a battery. A passive RFID tag is an RFID tag powered by an incoming radio frequency signal. The term "collision" is well understood in the art (see, for example, page 7 of Microchip Technology Inc., microID 13.56 MHz RFID System Design Guide (2004)) as simultaneous data signals from two or more active or passive RFID tags which interfere with each other ("collide") at the RFID reader. Thus, the term "non-anti-collision RFID tag" means an RFID tag whose data signal will collide with and interfere with the data signal from another non-anti-collision RFID tag at the RFID reader. Since the RFID tags 23c and 24c are non-anti-collision tags and since the RFID tags 23c and 24c are together in the capsule system 21c/22c, the data signals 29c from the RFID tags 23c and 24c collide at the reader 26c. A computer or microprocessor system 27c is provided for data storage and manipulation.

Figure 24:
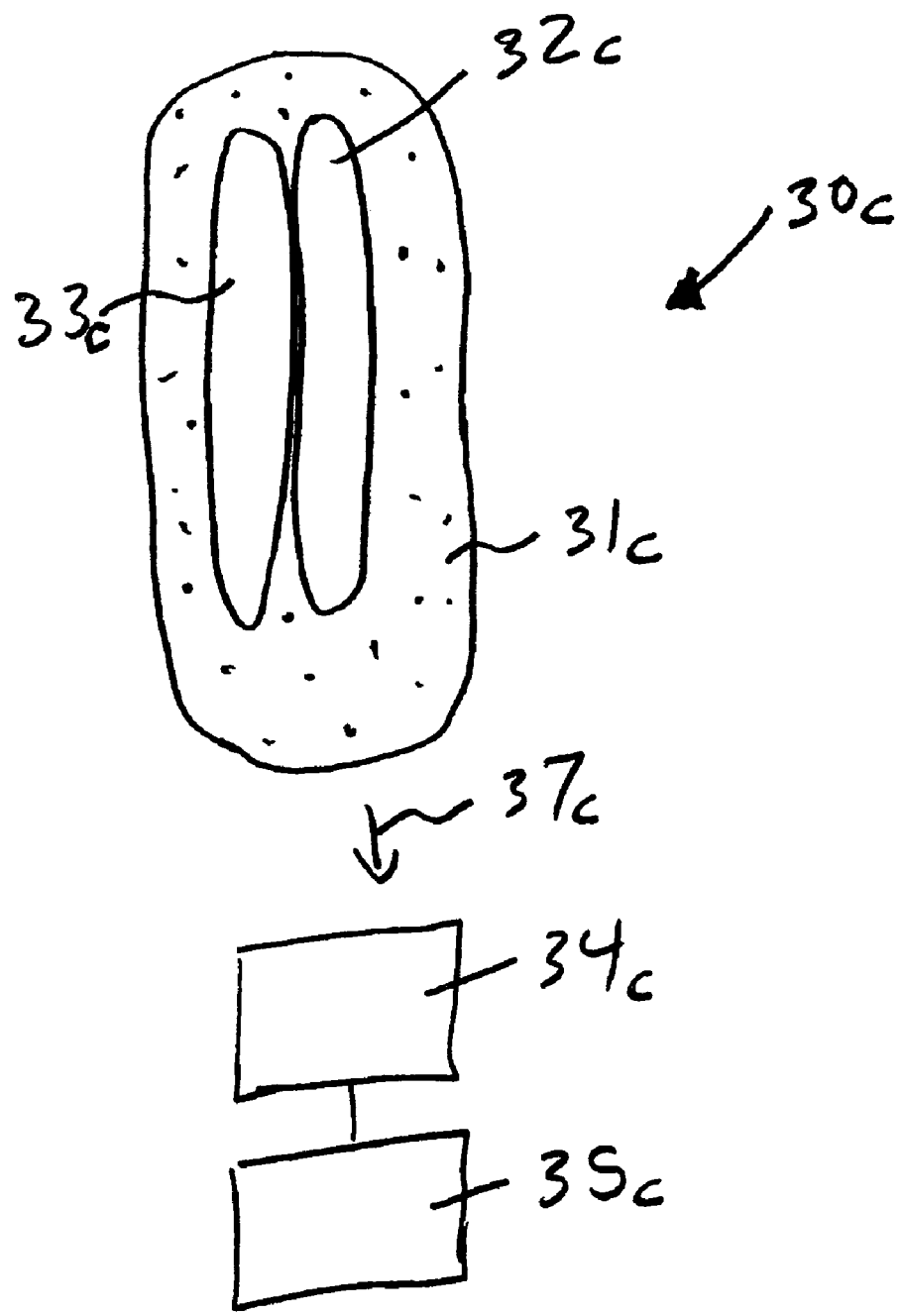
FIG. 24 shows a cross-sectional view of a tablet containing a pair of passive non-anti-collision RFID tags being interrogated by an RFID reader.

Referring now to FIG. 24, therein is shown shows a cross-sectional view of a tablet 30c containing a drug formulation 31c, a first non-anti-collision active RFID tag 32c, a second non-anti-collision active RFID tag 33c, so that if the RFID tags 32c and 33c are interrogated by RFID reader 34c before the tablet 30c disperses in the gastrointestinal system, the data signal 37c of the RFID tags 32c/33c "collide" at the reader 34c. A computer or microprocessor system 35c is provided for data storage and manipulation.

Figure 25:
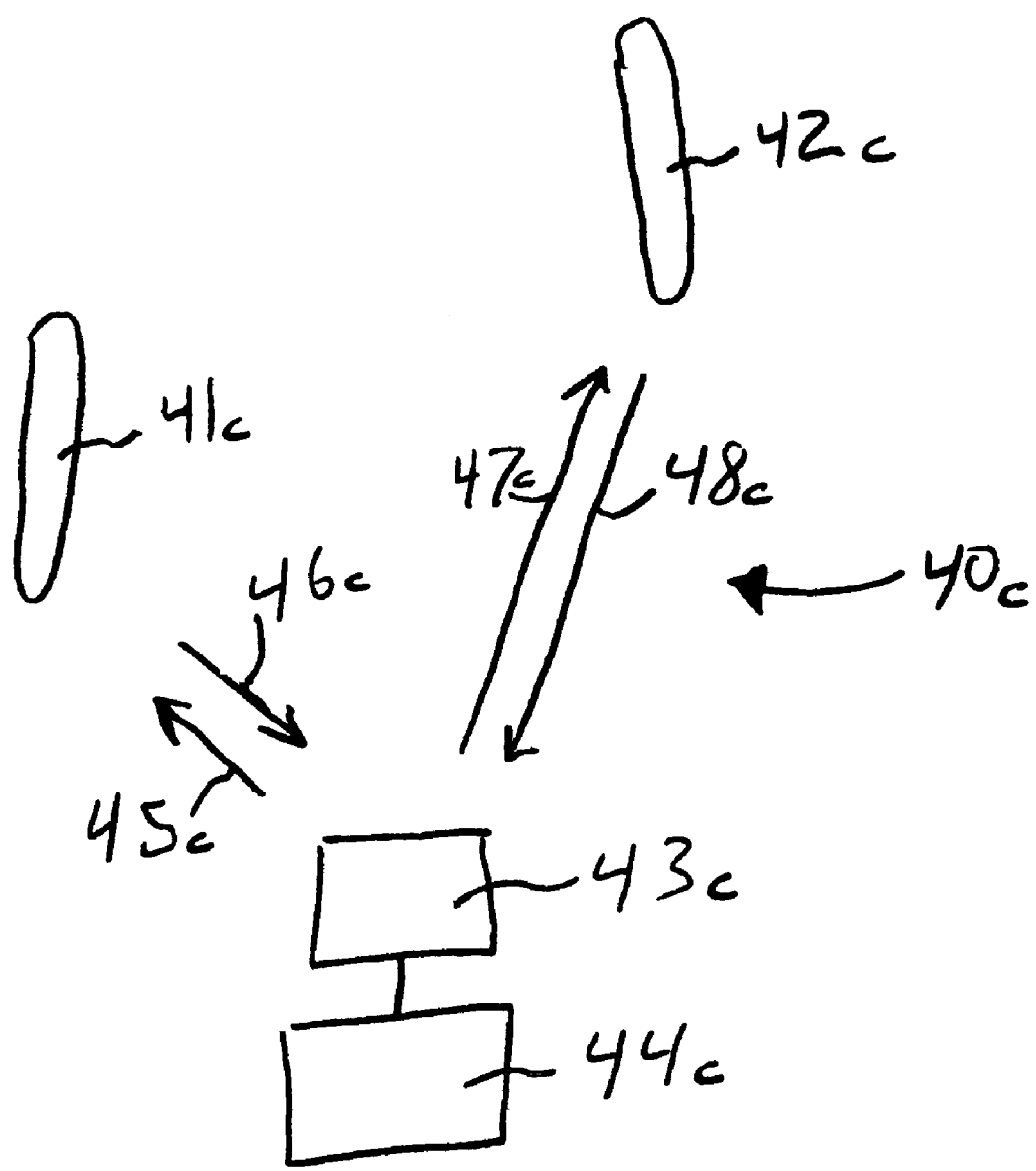
FIG. 25 shows a spaced apart pair of passive non-anti-collision RFID tags being interrogated by an RFID reader.

Referring now to FIG. 25, therein is shown a spaced apart pair of passive non-anti-collision RFID tags 41c and 42c (for example if they are separated in the gastrointestinal system) being interrogated by energizing/command signal 45c/47c from an RFID reader 43c. The RFID tags 41c and 42c produce data signals 46c and 48c to be received by the reader 43c. The RFID tag 41c is sufficiently closer to the reader 43c than the RFID tag 42c, such that the data signals 46c and 48c can be differentiated by the reader 43c. A computer or microprocessor system 44c is provided for data storage and manipulation.

Preferably, a pair of active or passive non-anti-collision RFID tags are used in the instant invention. However, it should be understood that more than two such RFID tags can be used. Each non-anti-collision RFID tag is preferably encoded to identify (via its data signal) the drug type, dose and lot number. The specific non-anti-collision RFID tags used in the instant invention are not critical. However, it is preferred that the RFID tag be encapsulated with an inert material such as glass.

EXAMPLE 1

A series of six uniquely coded glass encapsulated animal permanent identification RFID tags (Stoelting Company, Wooddale Ill.) are covered with ferrite rings (National Magnetics Group, Bethlehem Pa.) and placed in gelatin capsules with a simulated drug formulation consisting of food grade lactose (substantially as shown in FIG. 1). The capsules are each interrogated with a portable RFID reader (Allflex ISO Compatible RF/ID Portable Reader Model No. 930002-001) but the reader indicates "No Tag Found". The capsules are placed in a series of one liter beakers containing 900 mL of USP Simulated Gastric Fluid at 37 degrees Celsius with agitation. The capsules disperse and the reader held at a distance of about 10 centimeters from each RFID tag responds "Tag Found" at the following times: 1.50, 1.80, 1.85, 1.87, 1.88 and 1.95 minutes.

EXAMPLE 2

A series of six uniquely coded glass encapsulated animal permanent identification RFID tags (Stoelting Company, Wooddale Ill.) are covered with ferrite rings (National Magnetics Group, Bethlehem Pa.) and placed in gelatin capsules with a simulated drug formulation consisting of food grade lactose (substantially as shown in FIG. 1 except that three ferrite rings are used). The capsules are each interrogated with a portable RFID reader (Allflex ISO Compatible RF/ID Portable Reader Model No. 930002-001) but the reader indicates "No Tag Found". The capsules are placed in a series of one liter beakers containing 900 mL of USP Simulated Gastric Fluid at 37 degrees Celsius with agitation. The capsules disperse and the reader held at a distance of about 10 centimeters from each RFID tag responds "Tag Found" at the following times: 1.58, 2.22, 2.33, 3.25, 3.50 and 7.92 minutes.

EXAMPLE 3

A series of uniquely coded glass encapsulated animal permanent identification RFID tags (Stoelting Company, Wooddale Ill.) are covered with a pair of ferrite rings (National Magnetics Group, Bethlehem Pa.) and placed in gelatin capsules with a simulated drug formulation consisting of food grade lactose (substantially as shown in FIG. 1). Four healthy adult beagle dogs are dosed orally with a single capsule containing the RFID tags and ferrite rings. To read radio signals from the RFID tags, the receiver (Stoelting Company, Wooddale Ill.) is held manually within ~2 cm from the skin of the dog's abdominal region. The time for the first reading of the RFID tag after dissolution of the capsule and release of ferrite sleeves is determined at 1-minute intervals until the first reading is successfully achieved. Subsequent signals are read over time (1,2,4, 8 and 24 hours) thereafter until the RFID tags and ferrite rings passed through the gastrointestinal (GI) tract to be recovered from the collected feces. The time for the RFID tags and ferrite rings to pass through the GI tract and its appearance in the feces is also monitored at each collection interval (e.g., 0-24 and 24-48 hours). The dogs in an initial experiment have free access to feed, both prior to and after dosing. The dogs in a subsequent experiment fasted overnight (−16 hours) then had free access to feed 4 hours after dosing.

In the non-fasted dogs, radio signals are read within 10.3±5.1 minutes after dosing with individual variation of 4 to 16 minutes. Overnight fasting prior to dosing reduces the time to the first signal detection to 6±1 minutes after dosing with a lower individual variation between 5 and 7 minutes. The radio signals emitted by the RFID tag are easily read by the RFID reader at subsequent time points (1,2,4,8 and 24 hours after dosing) indicating location of the device within different regions of the GI tract. All of the devices are recovered from the feces within 24-30 hours from non-fasted and between 24-48 hours from the fasted dogs. Readability of the radio signals emitted from the RFID tags is within 2-3 cm from the animal body with the exception of one tag whose signals are strong enough to be read from 10-12 cm away from the body.

EXAMPLE 4

Two Stoelting Companion Animal Permanent Identification passive RFID tags (Allflex ISO Compliant FDX-B transponders; 12 mm implantable) together in a parallel fashion as shown in FIG. 23 are positioned in a gelatin capsule. The remainder of the capsule is filled with a drug composition. The capsule is interrogated with a portable RFID reader (Allflex ISO Compatible RF/ID Portable Reader Model No. 930002-001) but the reader indicates "No Tag Found" even at a 0 cm read distance. The capsule is placed in 900 mL of USP Simulated Gastric Fluid in a one liter beaker at 37 degrees Celsius with agitation. The capsule disperses after about two minutes and the reader held at a distance of about 10 centimeters from the one liter beaker responds "Tag Found". Six identical experiments are performed with the following times (in minutes:seconds) to successful read at a read distance of ca. 10 cm: 1:45, 2:02, 1:45, 2:10, 1:45, and 1:49.

EXAMPLE 5

A 433 MHz passive RFID tag is positioned in a gold foil modified gelatin capsule containing a drug formulation substantially as shown in FIG. 7. The capsule is interrogated with a portable RFID reader (Intermec IP3 Intellitag Portabe Reader) but the reader indicates "No Tag Found". The capsule is placed in 900 mL of USP Simulated Gastric Fluid in a one liter beaker at 37 degrees Celsius with agitation. The capsule disperses after about two minutes and the reader held at a distance of about 10 centimeters from the one liter beaker responds "Tag Found".

EXAMPLE 6

A 433 MHz active RFID tag having a conductivity switch is positioned in a large gelatin capsule containing a drug formulation substantially as shown in FIG. 15 (except the RFID tag is battery powered and the antenna is spiral wound in a dielectric). The capsule is placed in a plastic wire screen basket placed in the center of a 50 liter polyethylene tank containing 40 liters of USP Simulated Gastric Fluid at 37 degrees Celsius with agitation. A receiving dipole antenna is positioned at the bottom of the tank. Another receiving dipole antenna is positioned outside the tank. The gelatine capsule disperses in the simulated gastric fluid and the conductivity switch turns on the RFID tag which then transmits its 433 MHz signal. The signal strength received by the antenna in the tank is about 5 nanowatt. The signal strength received by the antenna outside the tank held against the tank is about 0.1 nanowatt. The signal strength received by the antenna outside the tank held 70 centimeters away from the tank is about 0.01 nanowatt. An arm held between the tank and the antenna slightly (2-3 dB) reduces the signal strength received by the antenna.

The minimum detectable signal strength received by the antenna outside the tank held even further from the tank is estimated to be about 0.0001 nanowatt. The signal strength received by the antenna outside the tank is only slightly dependent (a variation of about 1-5 dB) on the position of the antenna of the RFID tag.

CONCLUSION

While the instant invention has been described above according to its preferred embodiments, it can be modified within the spirit and scope of this disclosure. This application is therefore intended to cover any variations, uses, or adaptations of the instant invention using the general principles disclosed herein. Further, the instant application is intended to cover such departures from the present disclosure as come within the known or customary practice in the art to which this invention pertains and which fall within the limits of the following claims.

What is claimed is:

1. A device useful for oral drug delivery, comprising: (a) a capsule, tablet or pill which will disperse in the gastrointestinal system; (b) an RFID tag positioned in the capsule, tablet or pill, the RFID tag comprising an antenna; (c) an object selected from the group consisting of a magnet, a ferromagnetic object, a ferrite object and an electromagnetic shielding object, the object positioned within, over or adjacent the antenna of the RFID tag to alter the antenna characteristics of the RFID tag so that if the RFID tag is interrogated before the capsule, tablet or pill disperses in the gastrointestinal system, the response of the RFID tag is sufficiently altered or attenuated to determine that the capsule, tablet or pill has not dispersed in the gastrointestinal system and so that if the RFID tag is interrogated after the capsule, tablet or pill has dispersed in the gastrointestinal system, the object separates from the RFID tag so that the response of the RFID tag is sufficiently detectable to determine that the capsule, tablet or pill has dispersed in the gastrointestinal system.

2. The device of claim 1, wherein the object of element (c) disintegrates in the gastrointestinal system.

3. The device of claim 1, wherein the object of element (c) separates from the RFID tag in the gastrointestinal system.

4. The device of claim 1, wherein the RFID tag is selected from the group consisting of an active RFID tag and a passive RFID tag.

5. The device of claim 4, further comprising a drug formulation positioned in the tablet, pill or capsule.

6. A device useful for oral drug delivery, comprising: (a) a tablet, pill or capsule designed to disperse in the gastrointestinal system; (b) an RFID tag positioned in the tablet, pill or capsule, the RFID tag comprising a switch, the switch turning on or off in response to conditions in the gastrointestinal system so that if the RFID tag is interrogated before the tablet, pill or capsule disperses in the gastrointestinal system, the response of the RFID tag signifies that the capsule has not dispersed in the gastrointestinal system and so that if the RFID tag is interrogated after the tablet, pill or capsule disperses in the gastrointestinal system, the response of the RFID tag signifies that the tablet, pill or capsule has dispersed in the gastrointestinal system.

7. The device of claim 6, wherein the RFID tag is selected from the group consisting of an active RFID tag and a passive RFID tag.

8. The device of claim 7 further comprising a drug formulation positioned in the tablet, pill or capsule.

9. A device useful for oral drug delivery, comprising: (a) a capsule, tablet or pill designed to disperse in the gastrointestinal system; (b) a first non-anti-collision RFID tag positioned in the capsule; (c) a second non-anti-collision RFID tag positioned in the capsule, so that if the RFID tags are interrogated by an RFID reader before the capsule, tablet or pill disperses in the gastrointestinal system, the response of the RFID tags collide and so that after the dispersible material of the capsule has dispersed in the gastrointestinal system thereby allowing the first and second non-anti-collision tags to separate from each other, then the response of the RFID tags is sufficiently different from each other to determine that the capsule has dispersed in the gastrointestinal system.

10. The device of claim 9, wherein the RFID tag is selected from the group consisting of an active RFID tag and a passive RFID tag.

11. The device of claim 10, further comprising a drug formulation positioned in the tablet, pill or capsule.

* * * * *